(12) United States Patent
Alexander

(10) Patent No.: US 6,386,025 B2
(45) Date of Patent: *May 14, 2002

(54) TIRE INSPECTION EQUIPMENT AND METHOD

(75) Inventor: Bruce M. Alexander, Watkinsville, GA (US)

(73) Assignee: Oliver Rubber Company, Findlay, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/907,248

(22) Filed: Jul. 17, 2001

Related U.S. Application Data

(63) Continuation of application No. 09/272,644, filed on Mar. 18, 1999, now Pat. No. 6,269,689.
(60) Provisional application No. 60/093,758, filed on Jul. 22, 1998.

(51) Int. Cl.[7] .................. G01N 29/04; G01M 17/02
(52) U.S. Cl. ............................................. 73/146
(58) Field of Search ............................ 73/146, 146.2

(56) References Cited

U.S. PATENT DOCUMENTS

| 1,779,907 | A | * | 10/1930 | Dye | |
|---|---|---|---|---|---|
| 3,882,717 | A | * | 5/1975 | McCauley | 73/67.8 |
| 4,274,289 | A | * | 6/1981 | Wiess et al. | |
| 4,297,876 | A | * | 11/1981 | Weiss | 73/146 |
| 4,327,579 | A | * | 5/1982 | Weiss | 73/146 |
| 4,372,366 | A | * | 2/1983 | Dugger | |
| 4,516,068 | A | * | 5/1985 | Hawkinson, Jr. et al. | |
| 4,520,307 | A | * | 5/1985 | Weiss et al. | |
| 4,670,289 | A | * | 6/1987 | Miller, III | 73/146 |
| 4,918,976 | A | * | 4/1990 | Fogal, Sr. | 73/40.7 |
| 4,936,138 | A | * | 6/1990 | Cushman et al. | 73/146 |
| 4,969,350 | A | * | 11/1990 | Fogal, Sr. | 73/40.7 |
| 5,095,744 | A | * | 3/1992 | Macecek et al. | 73/146 |
| 6,269,689 | B1 | * | 8/2001 | Alexander | 73/146 |

FOREIGN PATENT DOCUMENTS

| EP | 0 392 859 A2 | 10/1990 | C01M/17/02 |
|---|---|---|---|
| EP | 0 440 847 A1 | 8/1991 | G01N/23/18 |

OTHER PUBLICATIONS

International Search Report for PCT/US99/14479 Dec. 10, 1999.

* cited by examiner

Primary Examiner—Eric S. McCall
(74) Attorney, Agent, or Firm—Baker Botts L.L.P.

(57) ABSTRACT

Apparatus and methods are provided for inspection of a tire for hidden irregularities and defects. The apparatus includes a remotely located control console to protect electronic components from contamination and debris associated with tire retreading and from mechanical vibration associated with handling and inspecting used tire casings. The apparatus includes a tire supporting and rotating assembly, a receiver control assembly, a moveable transmitter assembly for directing energy against a tire and a movable receiver assembly to receive energy passing through the tire. Components of the mechanical system used to control movement of the receiver assembly are spaced from components of the mechanical system which support and rotate the tire.

14 Claims, 12 Drawing Sheets

TIRE INSPECTION EQUIPMENT AND METHOD

CROSS REFERENCE TO RELATED APPLICATIONS

This application is a continuation from U.S. patent application Ser. No. 09/272,644, filed by Bruce M. Alexander on Mar. 18, 1999, and entitled "Tire Inspection Equipment and Method," now U.S. Pat. No. 6,269,689 which claims the benefit of provisional application Ser. No. 60/093,758 filed Jul. 22, 1998, and entitled "Tire Inspection Equipment and Method."

RELATED APPLICATIONS

TECHNICAL FIELD OF THE INVENTION

The present invention relates to improved tire inspection equipment, and more particular to equipment for inspecting used tires prior to retreading.

BACKGROUND OF THE INVENTION

Various types of equipment and procedures are currently used to inspect new tires and used tires. Such inspections are preferably conducted to find hidden irregularities or defects prior to retreading used tire casings. Economic loss occurs from retreading a damaged tire casing and later scrapping the resulting retread tire. Even greater loss may occur from potential safety hazards associated with using a retread tire having a damaged tire casing.

Most modern tires used on trucks and automobiles have multiple steel cords integrally molded within the associated tire casing. Work hardening of the steel cords may occur from operating the associated tire with less than the recommended air pressure. This type of defect in a used tire casing is sometimes referred to as a "zipper." Catastrophic failure may occur from retreading a used tire casing with damaged steel cords. For example, a new tire or a retread tire, after mounting on a tire rim, is often over pressurized to set or seal the associated tire beads within the rim. During over pressurization, catastrophic failure may occur in the vicinity of the damaged steel cords. As a result of such potential hazards, most major fleet tire dealers require inspection of used tire casings prior to retreading.

Although substantial efforts have been made to minimize dust, debris and other contamination associated with retreading used tires, tire inspection equipment must operate in an environment which is less than ideal for modern electronic components. Also, tire inspection equipment is frequently subject to significant mechanical vibration during handling and rotation of used tire casings. Contamination of electronic components and/or damage to electrical wiring and electrical circuits may reduce the overall operating efficiency of some types of tire inspection equipment.

Examples of tire inspection equipment and techniques are shown in U.S. Pat. No. 4,936,138 entitled Method And Apparatus For Tire Inspection and U.S. Pat. No. 4,520,307 entitled High-Voltage Tire Testing Apparatus. For many years Oliver Rubber Company located at P.O. Drawer 1827, Athens, Ga. 30603-1827 has manufactured and sold Tuff-Scan® and Wide-Scan® ultrasonic tire casing inspection equipment.

SUMMARY OF THE INVENTION

In accordance with teachings of the present invention, substantially enhanced tire inspection equipment and methods are provided. One aspect of the present invention includes tire inspection equipment having a movable energy transmitter assembly and a movable energy receiver assembly to detect energy from the transmitter assembly passing through a tire casing. For some applications sonic or ultrasonic energy may be used to find hidden defects or irregularities in a used tire casing. For other applications electromagnetic energy or a combination of electromagnetic and sonic or ultrasonic energy may be used.

Other aspects of the present invention include providing mechanical and electrical systems to coordinate movement of an energy transmitter assembly and an energy receiver assembly relative to each other for inspection of a tire casing. The mechanical and electrical systems cooperate with each other to allow inspection of a wide variety of tire sizes and types.

Technical benefits of the present invention include the ability to scan both the sidewalls and tread of a tire casing. Portions of the electrical system are preferably contained in an electronic console or control console remotely located from other mechanical components of the tire inspection system. The portions of the mechanical system used to move the receiver assembly relative to the transmitter assembly is preferably spaced from the portions of the mechanical system which support and rotate the tire casing during an inspection cycle. As a result of incorporating teachings of the present invention the possibility of damage to electrical and/or mechanical components from vibration associated with handling and rotating a used tire casing are minimized. Also, placing portions of the electrical system in a remotely located console will protect the associated electronic components from any contamination present in the tire retreading facility.

Further technical benefits of the present invention include a mechanical system which requires only one stroke setting to adjust movement of the transmitter assembly and receiver assembly to accommodate a specific size and type of tire casing. Existing tire inspection systems may be modified by adding mechanical and electrical components incorporating teaching of the present invention. Alternatively, new tire inspection equipment may be built with mechanical and/or electrical systems incorporating teachings of the present invention.

BRIEF DESCRIPTION OF THE DRAWINGS

For a more complete understanding of the present invention, and the advantages thereof, reference is now made to the following written description taken in conjunction with the accompanying drawings, in which:

FIG. 6 is a drawing showing the relationship of FIGS. 6A, 6B and 6C with each other;

DETAILED DESCRIPTION OF THE INVENTION

The preferred embodiments of the present invention and its advantages are best understood by referring to the FIGS. 1 through 9 of the drawings, like numerals being used for like and corresponding parts of the various drawings.

Figure 1:
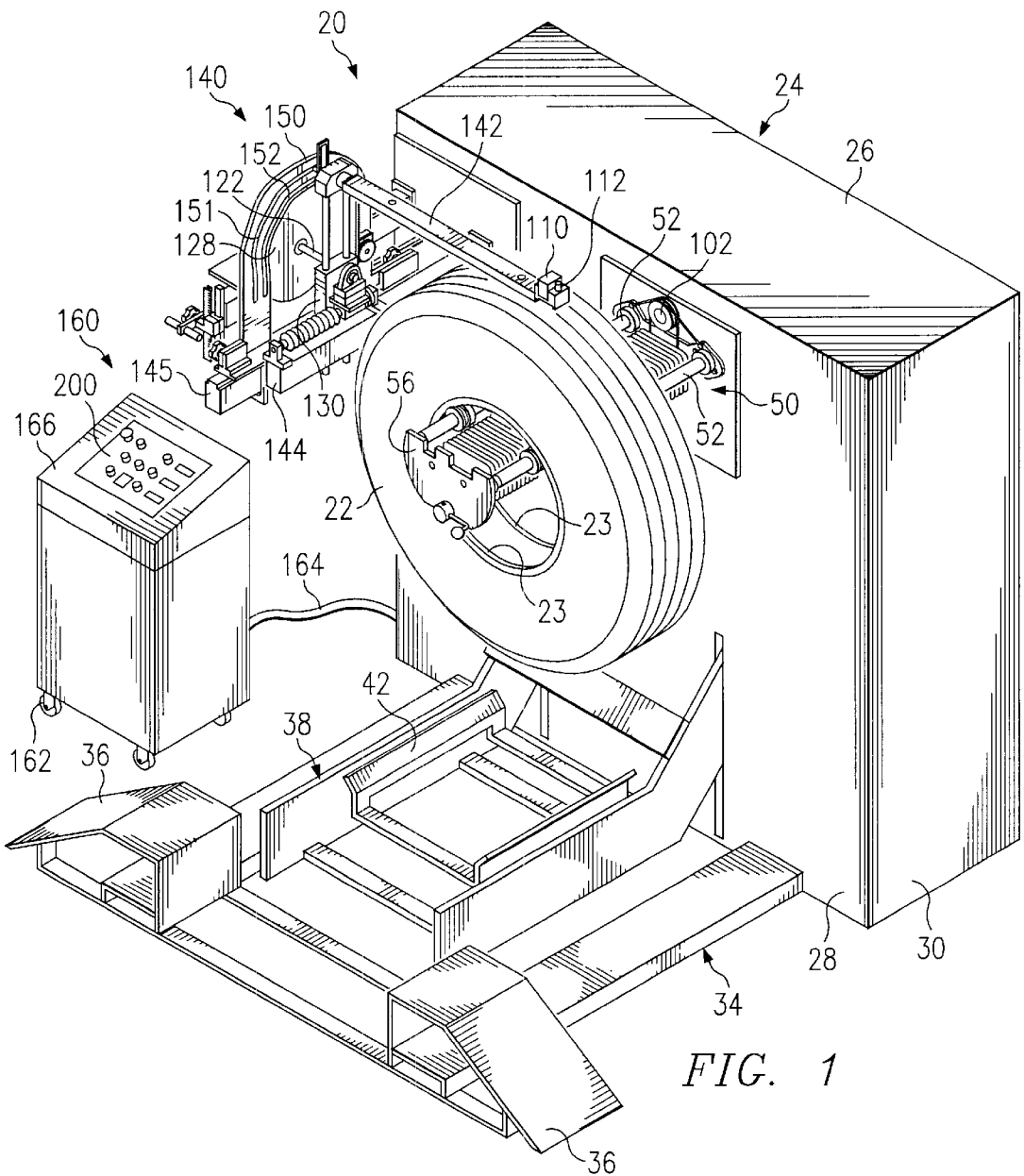
FIG. 1 is a schematic drawing showing an isometric view of one example of tire inspection equipment incorporating teachings of the present invention.

Tire inspection equipment 20 is shown in FIG. 1 with tire 22 in its normal position for rotation during an inspection cycle. Transmitter assembly 40, not expressly shown in FIG. 1, is preferably disposed within tire 22 to direct energy through tire 22 to receiver assembly 110. Receiver assembly 110 is mounted on control arm 142 which extends above tire 22. Tire inspection equipment 20 includes a mechanical system and an electrical system which cooperate with each other to control movement of transmitter assembly 40 and receiver assembly 110 relative to each other during an inspection cycle of tire 22. Various components of the mechanical system associated with controlling the movement of transmitter assembly 40 and receiver assembly 110 are shown in FIGS. 1, 2, 3A, 3B and 3C.

Tire inspection equipment 20 will typically be used to inspect a used tire casing prior to buffing. However, tire inspection equipment 20 may be satisfactorily used to inspect a used tire casing after buffing. Tire inspection equipment incorporating teachings of the present invention may also be used to inspect new tires and retread tires. Tire inspection equipment incorporating teachings of the present invention may be used at various stages during retreading of used tires and/or the manufacture of new tires depending upon desired quality control and inspection procedures.

Electrical and mechanical components associated with moving transmitter assembly 40 and receiver assembly 110 relative to each other and relative to tire 22 will be discussed later in more detail. U.S. Pat. No. 4,936,138 entitled Method and Apparatus for Tire Inspection contains detailed information concerning various mechanical and/or electrical components which may be satisfactorily used with tire inspection equipment incorporating teachings of the present invention.

Tire inspection equipment 20 includes first housing 24 which may be generally described as a relatively large, hollow enclosed structure. First housing 24 preferably includes top plate 26, front plate 28, a pair of side plates 30, bottom plate 32 and a back plate (not expressly shown). Base assembly 34 is preferably attached to the lower portion of front plate 28 and extends therefrom to support first housing 24. Base assembly 34 includes a pair of ramps 36 extending from opposite sides thereof. Lift assembly 38 is also attached to and extends from front plate 28. Hydraulic actuator 44 is preferably disposed within the interior of first housing 24 for use in raising and lowering lift assembly 38. Cradle 42 is slidably disposed within lift assembly 38 and may be positioned between ramps 36. Tire supporting and rotating assembly 50 and receiver control assembly 140 are mounted on the exterior of front plate 28.

Figure 2:
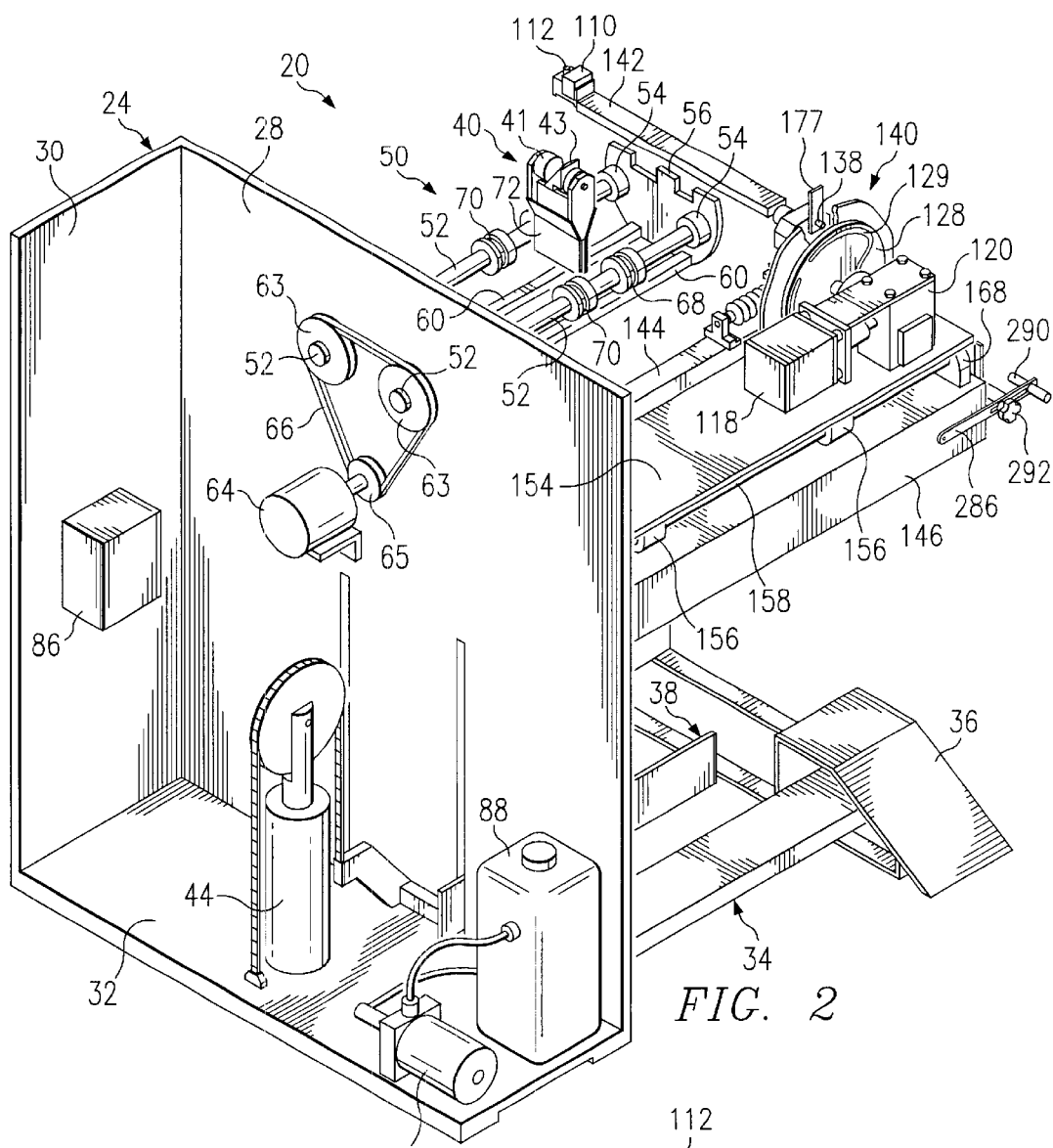
FIG. 2 is a schematic drawing with portions broken away showing the tire inspection equipment of FIG. 1 with a top panel, a back panel and one side panel removed.

Lift assembly 38 preferably has a first, lowered position as shown in FIGS. 1 and 2 and a second, raised position (not expressly shown). Cradle 42 also has a first, extended position between ramps 36 (not expressly shown) and a second, retracted position as shown in FIG. 1. When the inspection of tire 22 has been completed, receiver control assembly 140 will preferably move control arm 142 and receiver assembly 110 to a position (not expressly shown) between tire 22 and front plate 28. This position is sometimes referred to as the "home position."

Lift assembly 38 can only be activated when transmitter assembly 40 and receiver assembly 110 are in their respective home positions.

Figure 9:
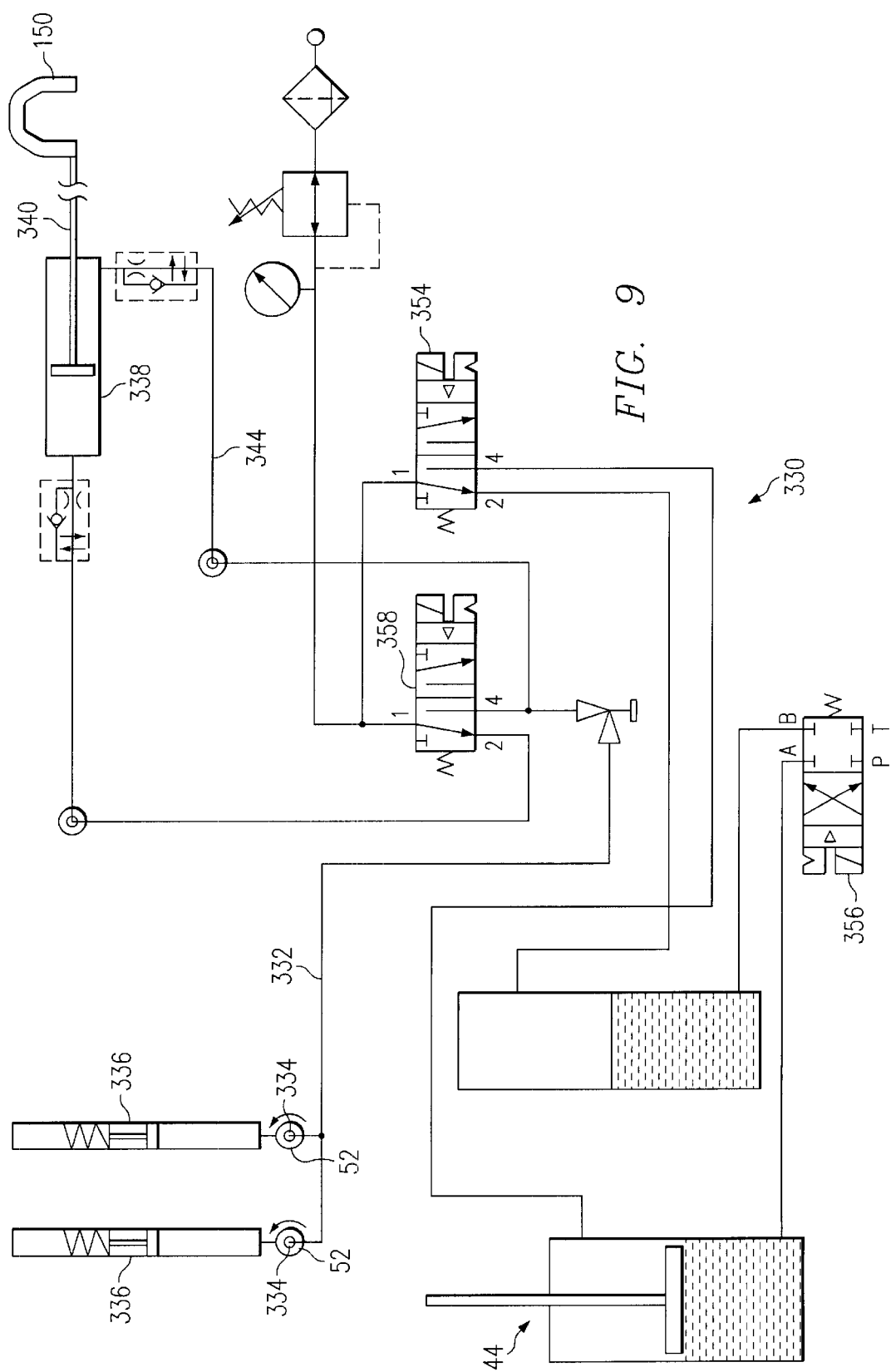
FIG. 9 is a schematic drawing showing a block diagram of a pneumatic/hydraulic control circuit satisfactory for use with the tire inspection equipment of FIG. 1.

Pedals 354 and 356 (not expressly shown in FIGS. 1 and 2 may be used to raise and lower cradle 38. Directional valve 358 in cooperation with pedals 354, 356 and their associated hydraulic control valves cooperate with each other along with other components of hydraulic-pneumatic control system 330 as best shown in FIG. 9 to prevent undesired movement of lift assembly 38 when control arm 142 and receiver assembly 110 are not in the home position.

With cradle 42 in its second position, lift assembly 38 may be raised to its second position. Cradle 42 and lift assembly 38 will engage and raise tire 22 a sufficient distance such that movement of cradle 42 to its first position will remove tire 22 from tire supporting and rotating assembly 50. Lift assembly 38 may then be lowered to its first position.

Since cradle 42 was moved to its first position, tire 22 may be rolled down one of the ramps 36. Another tire 22 may be rolled up one of the ramps 36 into cradle 42. Lift assembly 38 may then be moved to its second position (not expressly shown) to align tire supporting and rotating assembly 50 with the opening defined by beads 23 of tire 22. Cradle 42 with tire 22 resting therein may be moved to its second position. After tire 22 has been properly positioned relatively to tire support and rotating assembly 50, lift assembly 38 may be returned to its first position with cradle 42 in its second position as shown in FIG. 1. Tire 22 may then be inspected using tire inspection equipment 20 in accordance with teachings of the present invention. As previously noted, foot pedals 354, 356 and third associated control valves may be provided within base assembly 34 for use in raising and lowering lift assembly 38. See FIG. 9.

During an inspection cycle, tire 22 is supported by a pair of roller shafts 52 which extend through first bulkhead 51 attached to front plate 28 by bolts 53. One of the technical benefits of the present invention includes the ability to install or remove tire supporting and rotating assembly 50 from first housing 24 by engaging or releasing bulkhead 51 from front plate 28. As a result tire supporting and rotating assembly 50 may be used with existing tire inspection equipment such as shown in U.S. Pat. No. 4,936,138 or with new tire inspection equipment. A wide variety of mechanical fasteners in addition to bolts 53 may be satisfactorily used to releasably secure bulkhead 51 with front plate 28.

Roller shafts 52 preferably extend generally horizontally from first housing 24. Roller shafts 52 are also spaced from each other an appropriate distance to accommodate various sizes and types of tire casings. The outer end of each roller shaft 52 opposite from front plate 28 is preferably disposed within respective bearing blocks 54. See FIG. 2. Bearing blocks 54 are slidably disposed adjacently to end plate 56. As discussed later in more detail handle or elevation lever 84 may be used to raise and lower roller shafts 52 relative to bulkhead 51 and end plate 56.

A pair of supporting rods 58 also extend from bulkhead 51 and are attached to end plate 56. See FIG. 3A. For purposes of illustration, supporting rods 58 are not shown in FIG. 2. Supporting rods 58 cooperate with transmitter tower 72 and carriage assembly 74 to allow movement of transmitter assembly 40 within tire 22.

Figure 3A:
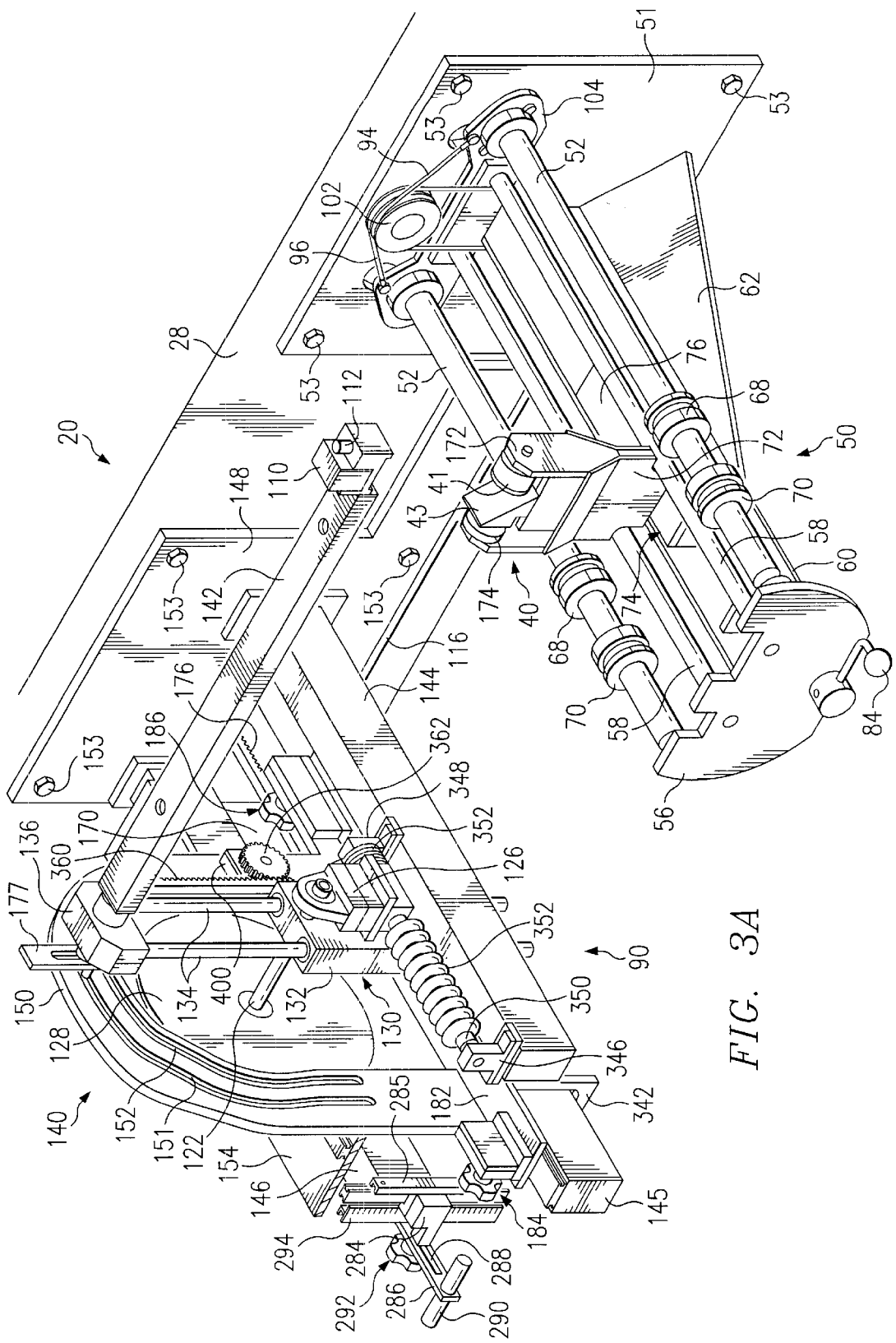
FIG. 3A is a schematic drawing with portions broken away showing an enlarged isometric view of various components of the mechanical system associated with the tire inspection equipment of FIG. 1.
Figure 3B:
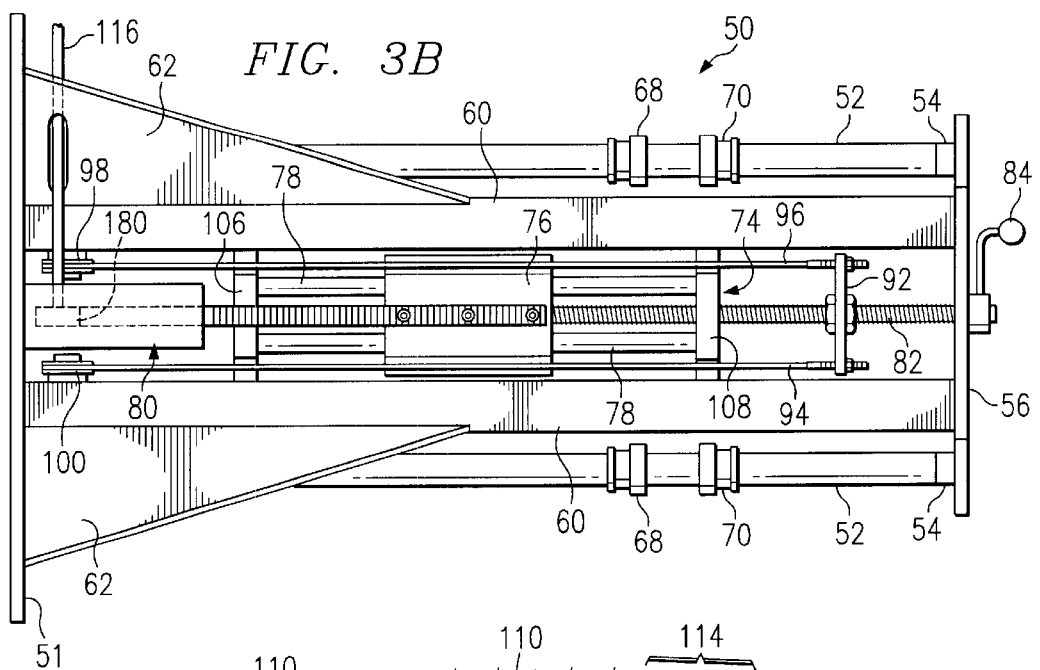
FIG. 3B is a schematic drawing with portions broken away showing a bottom view of a tire supporting and rotating assembly associated with the mechanical system of FIG. 3A.

A pair of angle irons 60 as best shown in FIG. 3B are securely attached to and extend between bulkhead 51 and end plate 56. Respective gusset members 62 are preferably attached to each angle iron 60 and bulkhead 51. Bulkhead 51, angle iron 60 and end plate 56 are securely attached to and do not move with respect to front plate 28 of first housing 24. Angle irons 60, gussets 62 and end plate 56 cooperate with each other to provide structural support for roller shafts 52 when tire 22 is mounted thereon.

As best shown in FIGS. 3A and 3B, handle 84 which may sometimes be referred to as an "elevation lever" preferably extends from end plate 56. Handle 84 rotates lead screw 82 which extends from front plate 56 to bulkhead 51. Connector 92 and wire ropes 94 and 96 are attached to lead screw 82 such that rotation of handle 84 will cause connector 92 to move longitudinally between bulkhead 51 and end plate 56. Wire ropes 94 and 96 extend from connector 92 over respective idler gears 98 and 100 to common idler gear 102. Wire ropes 94 and 96 are then connected to a respective roller shaft 52. The direction of rotation of handle 84 will determine if roller shafts 52 are raised or lowered relative to bulkhead 51. An indicator (not expressly shown) is preferably provided on front plate 56 such that roller shafts 52 may be properly positioned for the size and type of tire which will be mounted thereon. Thus, handle 84 may be rotated in the appropriate direction until the indicator displays an elevation number corresponding with the type and size of the tire mounted on roller shafts 52. Respective pivot plates 104 are provided at each end of roller shafts 58 adjacent to bulkhead 51. Wire ropes 94 and 96 are connected to respective pivot plates 104. Movement of roller shafts 52 generally describes an arc as they are raised and lowered by handle 84 and wire ropes 94 and 96.

As shown in FIG. 2, roller shafts 52 extend through bulkhead 51 and are preferably attached to respective sheaves 63. Electrical motor 64, pulley 65 and drive belt 66 are provided to rotate roller shafts 52 with tire 22 mounted thereon. Control box 86, marker fluid reservoir 88 and marker fluid pump 90 are preferably disposed within the interior of first housing 24. Various components of hydraulic/pneumatic control system 330 (See FIG. 9) are also contained within first housing 24. The function of these components will be discussed later in more detail.

Prior to initiating an inspection cycle, tire 22 is preferably centered on roller shafts 52 such that tire 22 will have an axis of rotation (not expressly shown) which is generally parallel with and remains at a constant distance from roller shafts 52. Also, tire 22 is preferably centered on roller shafts 52 such that a plane (not expressly shown) will extend through tire 22 perpendicular to the associated axis of rotation at a fixed distance spaced from and parallel with front plate 28.

As discussed in more detail in U.S. Pat. No. 4,936,138, centering may be accomplished by using respective inner and outer spacer rings 68 and 70. Multiple spacer rings may be provided on roller shafts 52 to accommodate tires of different sizes and types. Spacer rings 68 and 70 may also be referred to as "bead spreaders" since they preferably engage respective beads 23 of tire 22. One of the functions of hydraulic/pneumatic control system 330 includes opening and closing bead spreaders or spacer rings 68 and 70.

As shown in FIG. 9, air is supplied from control line 332 to respective rotary couplings 334 attached to the end of each roller shaft 52 disposed within the interior of first housing 24. Air pressure flows from control line 332 through respective rotary coupling 334 and a hollow bore (not expressly shown) formed in each roller shaft 52 to respective pneumatic cylinders 336. Spacer rings 68 and 70 are activated by respective pneumatic cylinders 336 to releasably engage beads 23 of tire 22.

For the embodiment of the present invention as shown in FIGS. 1–5, transmitter assembly 40 preferably includes transmitter transducer 41 and rotatable mirror 43. Transmitter transducer 41 preferably transmits collimated bursts or pulses of acoustic energy toward rotatable mirror 43. Depending upon the intended application for tire inspection equipment 20, transmitter transducer 41 may be selected to transmit either sonic or ultrasonic energy. A wide variety of commercially available sonic and ultrasonic transducers may be satisfactorily used with the present invention. The term "acoustic" is used to include both sonic and ultrasonic energy as appropriate for the specific type of tire inspection equipment.

Bursts or pulses of acoustic energy are directed at the interior surface of tire 22 by transmitter assembly 40. Receiver assembly 110 is disposed on the exterior of tire 22 to receive portions of the acoustic energy passing therethrough. The movement and orientation of rotatable mirror 43 are preferably coordinated with movement of transmitter assembly 40 and receiver assembly 110 in accordance with teachings of the present invention. Each burst of acoustic energy is preferably directed toward relatively small inspection areas 46. See FIG. 4. As discussed later in more detail, the portion of each acoustic energy burst received by receiver assembly 110 will be evaluated to find hidden irregularities or defects within tire 22.

The movement of transmitter assembly 40 is preferably controlled so that bursts of acoustic energy will scan the interior surface of tire 22 from one sidewall to the other sidewall as tire 22 is rotated relative to transmitter assembly 40. During a complete inspection cycle of tire 22, multiple overlapping inspection areas 46 will be evaluated. When a possible defect or irregularity is noted in an inspection area 46, marking device 112 will be activated to indicate the location of the possible irregularity or defect in tire 22. However, a mark does not always mean that tire 22 has a defect. Therefore, properly trained personnel must observe the operation of tire inspection equipment 20 and evaluate the significance of any marks placed on the exterior of tire 22.

As discussed later in more detail, control arm 142 will move receiver assembly 110 over the exterior of tire 22 in an arc which corresponds generally with the exterior of tire 22. As transmitter assembly 40 scans the interior of tire 22, receiver assembly 110 is preferably maintained aligned with transmitter assembly 40 to receive portions of collimated bursts of acoustic energy passing through tire 22. The movement of transmitter assembly 40 is also controlled to assure that each pulse of the collimated acoustic energy strikes the interior surface of tire 22 at substantially a right angle. Receiver assembly 110 is preferably positioned to detect or receive the portion of each acoustic pulse leaving the exterior surface of tire 22 at approximately a right angle.

As discussed later in more detail, receiver control assembly 140 includes first stepper motor 118 which, in cooperation with other components of receiver control assembly 140, moves receiver assembly 110 around the perimeter of tire 22. Transmitter assembly 40 is mounted on transmitter tower 72 extending upwardly from the carriage assembly 74. The axis of a rotation for mirror 43 is preferably parallel with the axis of rotation for control arm 142. Mirror 43 and transmitter transducer 41 are attached to platform member 172 on transmitter tower 72. Mirror 43 is connected for rotation to a transmitter stepper motor 174 (sometimes referred to as "second stepper motor 174") which is electrically connected to and controlled by first stepper motor 118. (See FIG. 7). Thus, there is a fixed relationship between rotation of control arm 142 and rotation of mirror 43.

Figure 4:
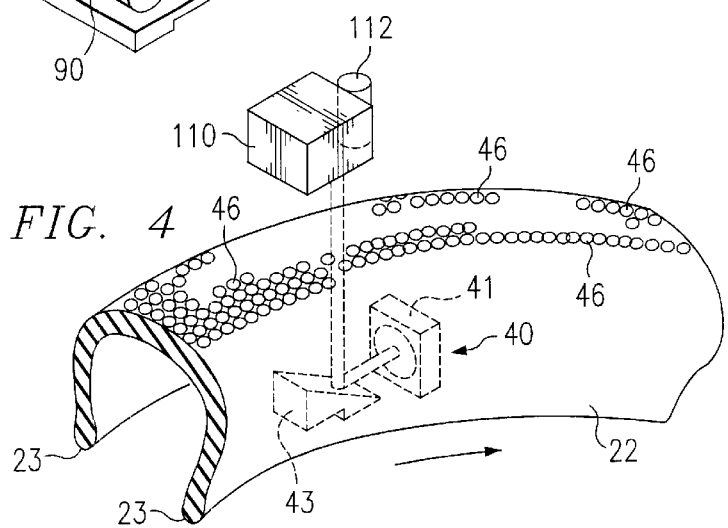
FIG. 4 is a schematic drawing in section and in elevation with portions broken away showing a transmitter assembly and a receiver assembly inspecting a tire casing in accordance with teachings of the present invention.

FIG. 4 shows a typical tire cross-section of tire 22 during an inspection cycle with beads of 23 held slightly apart by spacer rings 68 and 70. Receiver control assembly 140 and control arm 142 preferably retain receiver assembly 110 at the appropriate position on the exterior of tire 22 corresponding with the orientation and position of mirror 43 relative to the interior of tire 22.

Figure 5:
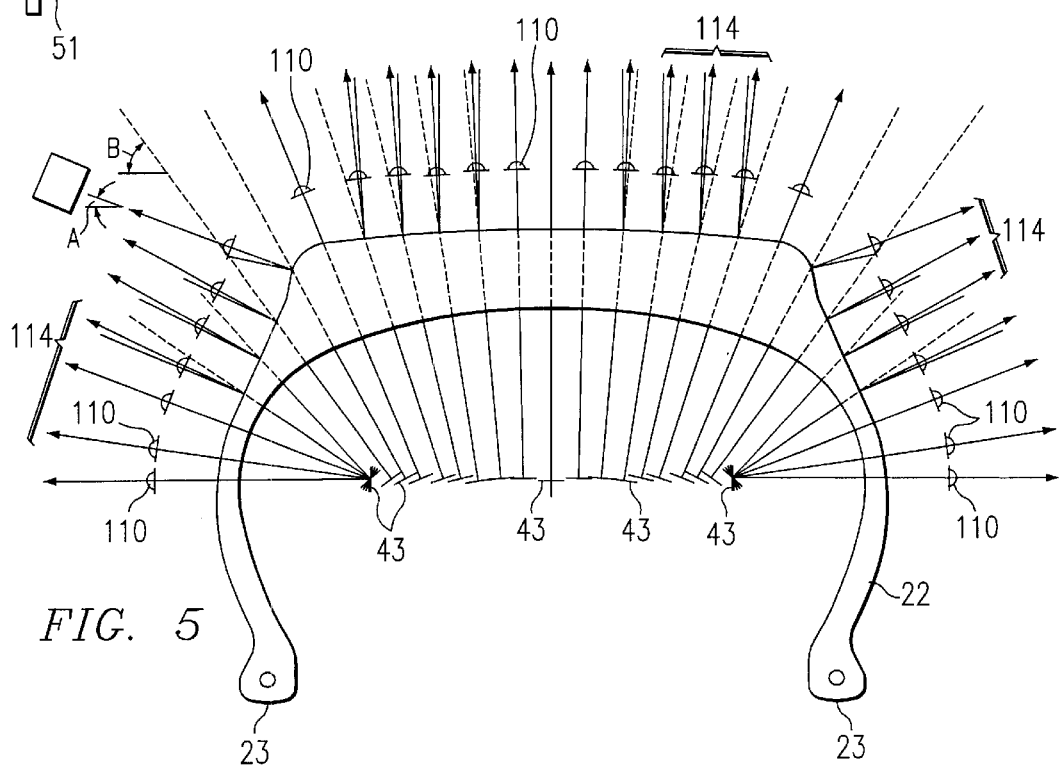
FIG. 5 is a schematic drawing in section with portions broken away showing a series of positions for the transmitter assembly and receiver assembly of FIG. 4 during a typical tire inspection cycle using teachings of the present invention.

FIG. 5 shows various positions of mirror 43 and receiver assembly 110 as transmitter assembly 40 scans the interior of tire 22 during a typical inspection cycle. Each arrow 114 represents a collimated burst of acoustic energy. Transmitter assembly 40 essentially moves along a straight line that extends generally between the sidewalls of tire 22. Since the collimated acoustic energy is preferably directed normal to the inside surface of tire 22, transmitter assembly 40 and control arm 142 generally translated a short distance laterally relative to tire 22 with each rotational step through the respective inspection arcs of mirror 43 and receiver assembly 110. Linear movement of transmitter assembly 40 is relatively large for most of the width of tire 22 which comprises the tread area, because the corresponding curvature of the inside tire surface is relatively small.

When transmitter assembly 40 approaches the end of its linear movement during an inspection cycle, such linear movement essentially ceases and mirror 43 only rotates during each remaining step increment of the inspection cycle to cover the sidewall area of tire 22. Coordinated lateral movement of transmitter assembly 40 and rotation of mirror 43 will cause each collimated acoustic pulse to impinge generally perpendicular against the inside surface of tire 22.

As previously noted, transmitter assembly 40 is preferably mounted on transmitter tower 72 which is in turn attached to carriage assembly 74. Transmitter tower 72 and carriage assembly 74 are slidably disposed within support rods 58 and angle irons 60. As best shown in FIG. 3B, carriage assembly 74 preferably includes linear bearing assembly 76 which is slidably disposed on a pair of rods 78. Linear bearings designated SB 12 (super pillow block) available from Thomson Industries, Inc. in Fort Washington, N.Y., may be satisfactorily used with the present invention. Carriage blocks 106 and 108 are spaced from each other and are attached to and extend between angle irons 60. Rods 78 are in turn attached to and extend longitudinally between carriage blocks 106 and 108.

Linear bearing assembly 76 is also attached to rack and pinion assembly 80. As discussed later in more detail, receiver control assembly 140 includes rack 176 and pinion gear 178. See FIG. 3C. Shaft 116 extends between and is rotatably connected with rack and pinion assembly 80 and pinion gear 178. Depending upon the size and type of tire mounted on roller shafts 52, shaft 116 may be rotated as required to maintain the desired relationship between transmitter assembly 40 within the interior of tire 22 and receiver assembly 110 disposed on the exterior of tire 22. Shaft 116 may be used to adjust the position of transmitter tower 72 and transmitter assembly 40 as appropriate for the size and type of tire 22 which will be inspected by tire inspection equipment 20.

Various components associated with receiver control assembly 140 are preferably mounted on supporting beams 144, 145 and 146 which extend generally horizontally from first housing 24. One end of supporting beams 144, 145 and 146 are respectively attached to second bulkhead 148. Bolts 153 or other suitable connectors are provided to releasably secure bulkhead 148 with front plate 28. One of the technical benefits of the present invention includes the ability to install or remove receiver control assembly 140 from first housing 24 by engaging or releasing second bulkhead 148 from front plate 28. As a result, receiver control assembly 140 may be used with existing tire inspection equipment such as shown in U.S. Pat. No. 4,936,138 or with new tire inspection equipment. The number and type of mechanical fasteners used to secure second bulkhead 148 with front plate 28 may be varied as appropriate for the intended use of receiver control assembly 140 and the associated tire inspection equipment 20.

Supporting beam 144 may sometimes be referred to as a "bearing beam." Supporting arm 145 may sometimes be referred to as a "track beam." Supporting beam 146 may sometimes be referred to as a "motor, gearbox beam." Various components associated with receiver control assembly 140 are slidably mounted on respective supporting beams 144, 145 and 146.

For purposes of describing the function of receiver control assembly 140 and transmitter carriage assembly 74 the terms "longitudinal" and "longitudinally" will be used with respect to linear movement along the length of supporting beams 144, 145 and 146 or supporting rods 58 as appropriate. Longitudinal movement in this direction corresponds generally with lateral movement between tire beads 23 when tire 22 is mounted on tire supporting and rotating assembly 50.

Figure 3C:
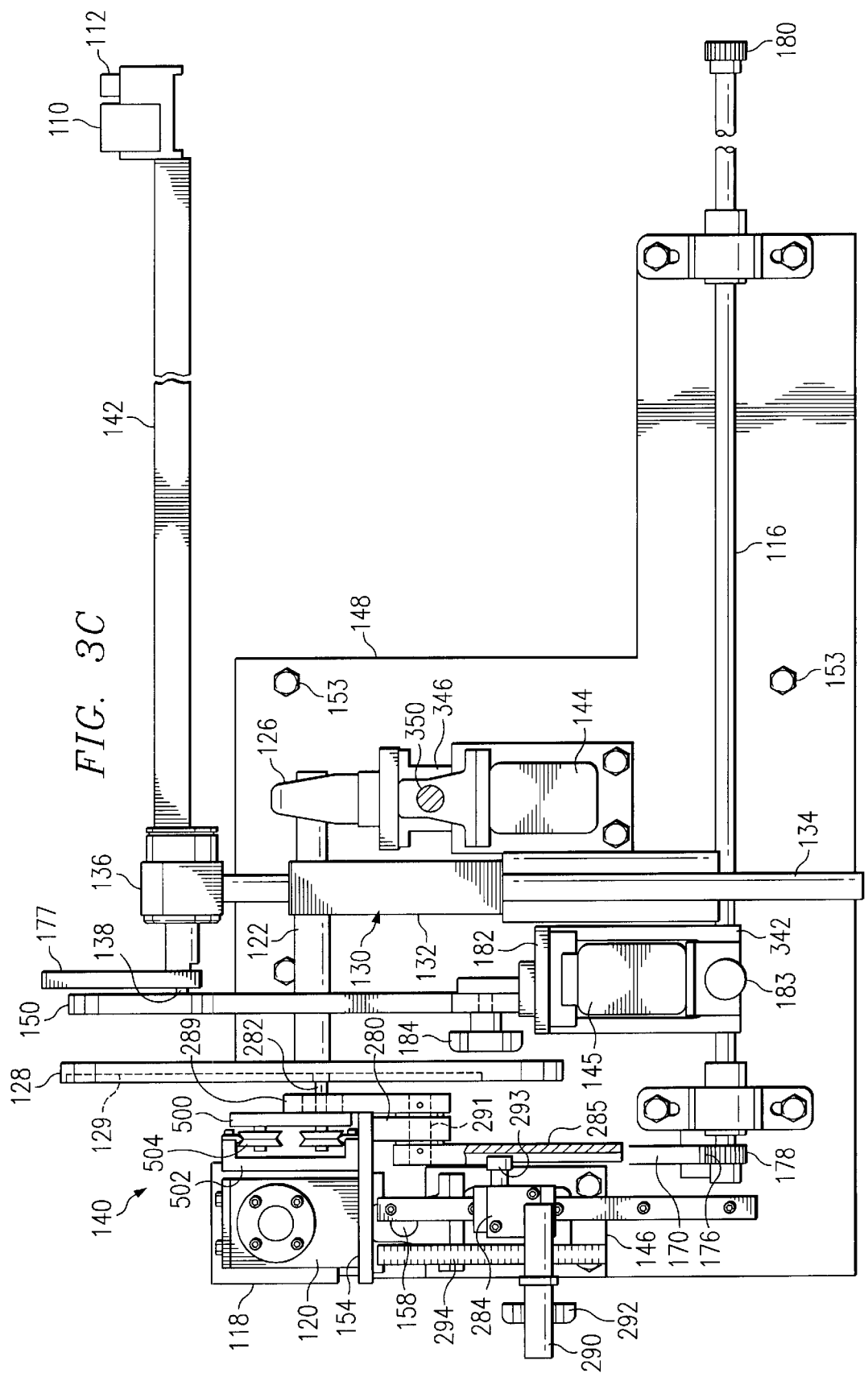
FIG. 3C is a schematic drawing in elevation with portions broken away showing an enlarged front view of a receiver control assembly associated with the mechanical system of FIG. 3A.

For the embodiment of the present invention as best shown in FIGS. 2 and 3C, stepper motor 118 and right angle gear reducer 120 are preferably mounted on plate 154. Plate 154 is in turn attached to linear bearings 156 which are slidably disposed on rod 158. Opposite ends of rod 158 are attached to supporting beam 146 by connectors 168. Only one connector 168 is shown in FIG. 2.

As best shown in FIG. 3C, plate 170 is preferably attached to the bottom of plate 154 opposite from first stepper motor 118. Plate 170 may sometimes be referred to as "a rack mount." Rack 176 is attached to the lower edge of plate 170 opposite from plate 154 and aligned with pinion gear 178. Gear 178 is in turn attached to shaft 116. Longitudinal movement of plate 154 relative to supporting beam 146 will result in corresponding longitudinal movement of plate 170. Engagement between the teeth on rack 176 and corresponding teeth on gear 178 results in rotation of shaft 116 in response to longitudinal movement of plate 154 and plate 170.

Gear 180 is preferably disposed on the opposite end of shaft 116 for engagement with rack and pinion assembly 80. Thus, longitudinal movement of plate 154 will result in movement of plate 170, rotation of shaft 116 and corresponding longitudinal movement of carriage assembly 74, transmitter tower 72 and receiver assembly 40.

Plate 182 is preferably slidably disposed on supporting beam 145. Mechanical stop 183 is preferably provided adjacently to the end of supporting beam 145 opposite from second bulkhead 148. See FIG. 3C. As best shown in FIG. 3A, clamp assemblies 184 and 186 are attached to plate 182 opposite from supporting beam 145. Clamp assemblies 184 and 186 are provided to releasably secure track 150 with plate 182. One of the technical benefits of the present invention includes remotely locating track 150 from tire supporting and rotating assembly 50 to minimize the possibility of damage to track 150 during loading and unloading of tire 22. Track 150 is a generally C-shape or U-shape configuration with grooves 151 and 152 formed therein. The function of track 150 and grooves 151 and 152 will be discussed later in more detail.

Pneumatic cylinder 338 as shown in FIG. 9 is preferably attached to supporting beam 145 opposite from plate 182. Piston rod 340 which extends from pneumatic cylinder 338 is preferably attached to connector 342. When pneumatic pressure is supplied from control line 344 to pneumatic cylinder 338, piston rod 340 will retract within pneumatic cylinder 338 which will result in movement of track 150 toward second bulkhead 148 and cause control arm 142 to move receiver assembly 110 to its "home" position.

As best shown in FIG. 3A, connectors 346 and 348 are preferably attached to the upper surface of supporting beam 144. Rod 350 extends between connectors 346 and 348. Second bearing assembly 126, which will be discussed later in more detail, is slidably disposed on rod 350. For the embodiment shown in FIG. 3A, a pair of collapsible bellows 352 is disposed on the exterior of rod 350 between bearing assembly 126 and connectors 346 and 348.

Receiver control assembly 140 as shown in FIGS. 1, 2, 3A and 3C, includes first stepper motor or receiver stepper motor 118 with an output shaft (not expressly shown) connected to right angle gear reducer 120. Output shaft 122 extends laterally from right angle gear reducer 120. First bearing assembly 124 is mounted on and attached to plate 154. Second bearing assembly 126 is attached to and slidably mounted on supporting beam 146. Output shaft 122 extends from right angle gear reducer 120 through first bearing assembly 124 and second bearing assembly 126. Cam or disk 128 is rotatably attached to output shaft 122 adjacent to first bearing assembly 124.

For some applications cam 128 may include one or more limit switches (not expressly shown) disposed on the side of cam 128 facing first stepper motor 118. For example, limit switches 187 and 185 shown in FIG. 7 may be placed on cam 128. One or more photo detectors or opto switches are preferably placed on plate 154 to sense when cam 128 has completed the desired amount of rotation. For some applications, three photocells or opto switches are provided to respectively slow down the rotation of first stepper motor 118, to stop rotation of first stepper motor 118, and to reverse the direction of rotation of first stepper motor 118.

Linear bearing assembly 130 is rotatably attached to output shaft 122 adjacent to second bearing assembly 126. Track 150 having a generally "C-shaped" configuration is preferably disposed between cam 128 and linear bearing assembly 130. As discussed later in more detail, cam 128, linear bearing assembly 130 and track 150 cooperate with each other to move control arm 142 and receiver assembly 110 through a generally elliptical path corresponding with the exterior of tire 22.

Linear bearing assembly 130 preferably includes housing 132 with a pair of rods 134 slidably disposed therein and extending therefrom. Connector 136 is attached to the extreme end of rods 134 opposite from housing 132. Control arm 142 is rotatably attached to and extends from connector 136 at approximately a ninety degree (90°) angle relative to rods 134. Connector 136 also includes one or more bearings to allow rotation of control arm 142 relative to connector 136.

The end of control arm 142 opposite from connector 136 supports receiver assembly 110 and marking device 112. Rotation of output shaft 122 by first stepper motor 118 will result in rotation of linear bearing assembly 130 and control arm 142 extending from rods 134. The axis of rotation for control arm 142 is substantially parallel with the axis of rotation for output shaft 122. The axis of rotation for mirror 43 within transmitter assembly 40 is also substantially parallel with the axis of rotation for output shaft 122 and control arm 142.

The generally elliptical path of control arm 142 and thus, receiver assembly 110 is made possible in part by engagement of follower 138 within the desired groove 151 or 152 formed in track 150. A portion of track 150 has been removed in FIG. 2 to better show follower 138. Engagement of follower 138 with respective track 151 or 152 will also cause control arm 142 to rotate relative to its longitudinal axis at the same time control arm 142 is moved around the exterior of tire 22 to maintain the desired orientation of receiver assembly 110 relative to transmitter assembly 40.

As best shown in FIG. 3A, rack 360 is preferably attached to connector 136 and extends therefrom in a direction generally parallel with rods 134. Potentiometer 400 (see also FIG. 6A) and pinion gear 362 (see FIG. 3A) are preferably mounted on and extend from housing 132. Rack 360 is engaged with pinion gear 362 such that linear movement of rods 134 relative to housing 132 will cause rack 360 to rotate pinion gear 362 and cause potentiometer 400 to generate a corresponding electrical signal.

Figure 3D:
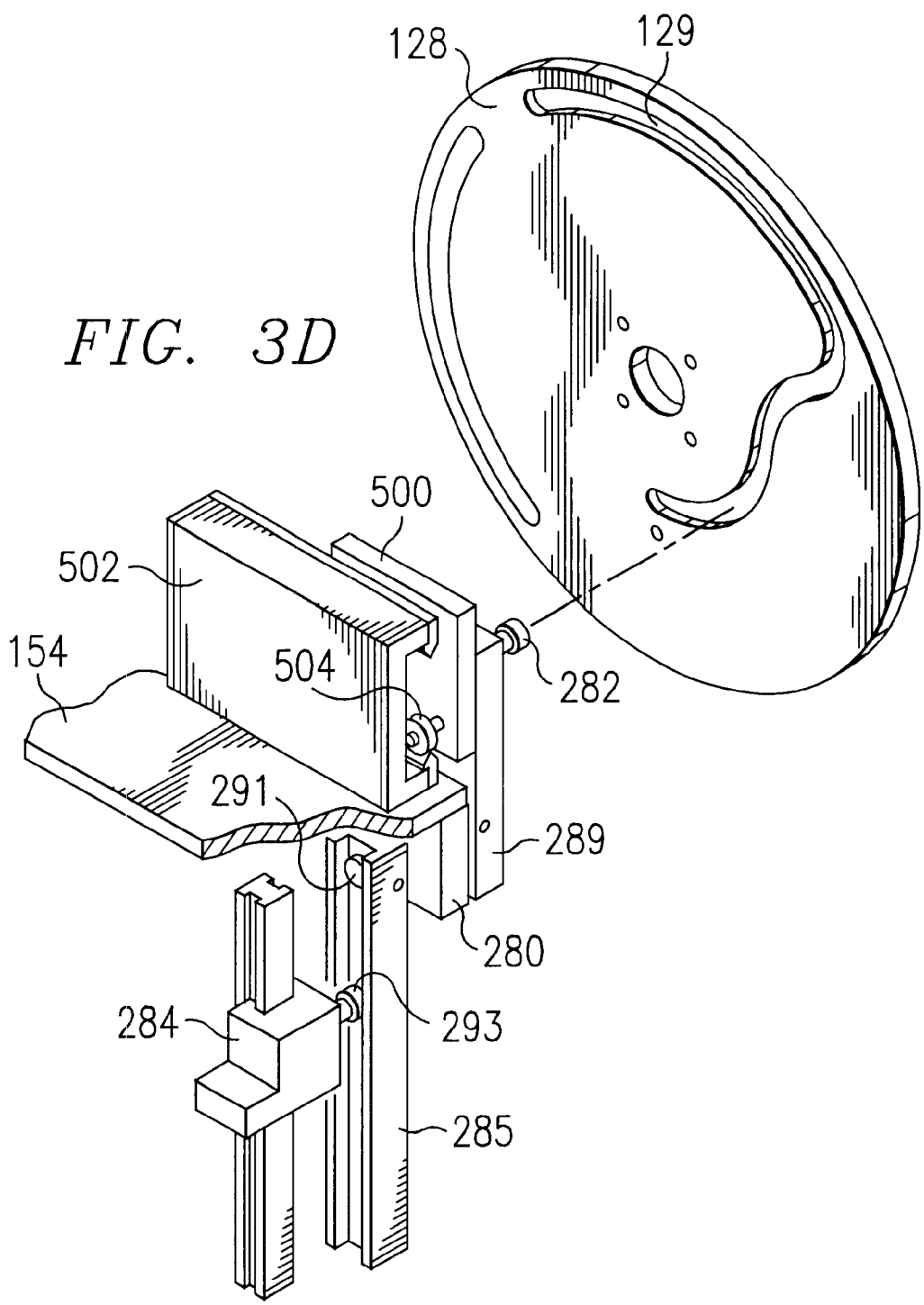
FIG. 3D is a schematic drawing with portions broken away showing an isometric view of a first pivot block, second pivot block, stroke actuator arm and cam associated with the tire inspection equipment of FIG. 1.

As best shown in FIGS. 3C and 3D, first pivot block 280 is preferably attached to the bottom of plate 154 near a terminal end of plate 154 opposite bulkhead 148. A second pivot block 284 is slidably disposed on the extreme end of supporting beam 146 opposite from second bulk head 148. A pivot pin 293 extends from second pivot block 284 and is slidably disposed within a track in stroke actuator arm 285. Second pivot block 284 allows adjustment of the stroke length by repositioning pivot pin 293 within the track of stroke actuator arm 285. Stroke actuator arm 285 is rotatably attached to a first side of first pivot block 280 by a connection pin 291. On the opposite side of first pivot block 280, connection pin 291 is coupled to connection arm 289 such that a movement in stroke actuator arm 285 results in a corresponding movement of connection arm 289. Stroke actuator arm 285 and connection arm 289 are fixably attached to connection pin 291 utilizing a pin (not expressly shown) which passes through connection pin 291 and into the associated arm. Cam pin 282 is attached to plate 500. Plate 500 provides vertical support for cam pin 282. Plate 500 is slidably disposed within track 502 using rollers 504 which are coupled to plate 500. Cam pin 282 passes through an elongated slot (not expressly shown) at the terminal end of connection arm 289. After passing through connection arm 289, cam pin 282 engages with a groove 129 formed in the portion of cam 128 facing first stepper motor 118.

As best shown in FIGS. 2, 3A and 3C, lever arm 286 is rotatably attached to the side of supporting beam 146 and extends longitudinally therefrom. Slot 288 is formed in lever arm 286. A pin (not expressly shown) preferably extends from second pivot block 284 and is disposed within slot 288. Handle 290 is preferably attached to the extreme end of lever 286. Clamp assembly 292 is provided to secure second pivot block 284 and lever 286 in the appropriate position for the size and type of tire mounted on roller shafts 52. The clamp assembly 292 also secures pivot pin 293 at a specific point in stroke actuator arm 285 based upon the position of lever 286.

By raising and lowering handle 290, lever arm 286 will rotate relative to supporting beam 146. Second pivot block 284 will thus be raised and lowered vertically as a result of its engagement with slot 288. The arm extending between first pivot block 280 and second pivot block 284 will move plate 154 to adjust the location of first pivot block 280 relative to supporting beam 146, and thus, the position of cam 128 and output shaft 122 relative to receiver assembly 40. Movement of pivot blocks 280 and 284 relative to each other, controls the shape of the elliptical path of control arm 142 during each inspection cycle. The precise position of first pivot block 280 and second pivot block 284 can be maintained by reference to scale 294 which is attached to the extreme end of supporting beam 146.

Since plate 154 is mechanically linked through plate 170, rack 176, shaft 116 and rack and pinion assembly 80 with carriage assembly 74, movement of lever 286 to adjust the position of first pivot block 280 will also adjust the position of transmitter tower 72 and thus transmitter assembly 40. Lever 286 and stroke actuator arm 285 connecting pivot blocks 280 and 284 with each other function as a "multiplier" to adjust the linear movement of plate 154 on supporting beam 146 in response to rotation of cam 128 by first stepper motor 118. For example, lever arm 286 may be positioned such that there is essentially no linear movement of either plate 154 or carriage assembly 74 during an inspection cycle. For other types and/or sizes of tires, lever 286 may be positioned such that plate 154 may move six or seven inches linearly along supporting beam 146 while control arm 142 rotates around the exterior of tire 22.

One of the technical benefits of the present invention includes providing a single lever arm 286 which can control the initial position of both output shaft 122 relative to supporting beams 146, 145 and 144 and also the position of transmitter tower 72 within tire 22. The same lever arm 286 may also be used to adjust the amount of linear movement by plate 154 and the other components mounted on supporting beams 144, 145 and 146 along with the linear movement of transmitter assembly 40 within tire 22 during an inspection cycle.

Cam 128 and stroke actuator arm 285 connecting first pivot block 280 and second pivot block 284 have previously been used on other types of tire inspection equipment sold by Oliver Rubber Company. Cams and other components satisfactory for use with the present invention may be obtained from Trienco, Inc. located in Montrose, Colo.

Follower 138 is sized to fit within grooves 151 and 152 which are formed within track 150. For tires of substantially different sizes and/or configurations, track 150 with different grooves 151 and 152 can be easily installed to provide the desired positioning of receiver assembly 110. Typically, a single track 150 will be satisfactory for use with multiple sizes and types of tires 22.

For some applications, first stepper motor 118 may operate at a rate of approximately eighteen steps per second with approximately 1.8° of rotation per step. Gear reducer 120, is selected to have a 30:1 reduction ratio so that output shaft 122 will rotate control arm 142 at an angular rate of approximately 1.1° per second. A programmable divider circuit (not shown) having a ratio less than 30:1 and electronically connected to first stepper motor 118 provides stepping pulses to second stepper motor 174 which rotates mirror 43 of transmitter assembly 40. Thus, mirror 43 will preferably rotate in synchronism at a slightly greater angular rate than the control arm 142. Transmitter assembly 40 angularly gains as the sidewalls of tire 22 are inspected to produce the inspection patterns of FIG. 5. Since mirror 43 and control arm 142 will preferably rotate at least one hundred and eighty degrees during one inspection cycle, each inspection cycle may be accomplished in about one hundred steps of first stepper motor 118 or approximately one hundred and eighty seconds.

At each of the ends of track 150, second stepper motor 174 is electronically temporarily inhibited by a non-reflective spot or flag 175 mounted on track 150 until receiver assembly 110 "leads" mirror 43 of transmitter assembly 40. Flag sensor 177 is mounted on connector 136 adjacent to follower 138 to detect flags 175. The net effect is that, as control arm 142 and receiver assembly 110 rotate through an arc of approximately one hundred and eighty degrees, the angle of mirror 43 is automatically controlled to produce the desired inspection pattern such as shown in FIG. 5.

At the beginning of each inspection cycle, control arm 142 is preferably positioned to its home position on one side of tire 22 adjacent to front plate 28. In the home position transmitter assembly 40 is at one end of its linear movement adjacent to the sidewall of tire 22 closest to front plate 28. Mirror 43 of the transmitter assembly 40 is in a substantially horizontal position. Accordingly, receiver assembly 110 on the control arm 142 is spaced directly outwardly from the sidewall of tire 22 nearest front plate 28 and is oriented to receive collimated acoustic energy from transmitter assembly 40 through tire 22.

As an inspection cycle commences, each step of first stepper motor 118 causes rotation of control arm 142 toward its other extreme position on the opposite side of tire 22. Rotation of output axis 122 causes rotation of linear bearing assembly 130. Cooperation between follower 138 and respective groove 151 or 152 in track 150 will cause rotation of control arm 142 relative to connector 136. Movement of rack 360 relative to pinion gear 362 results in potentiometer 400 applying a varying control voltage to processor 196 (See FIG. 6A) to adjust for processor delay according to any variation in the time an acoustic signal travels between transmitter assembly 40 and receiver assembly 110.

Figure 6A:
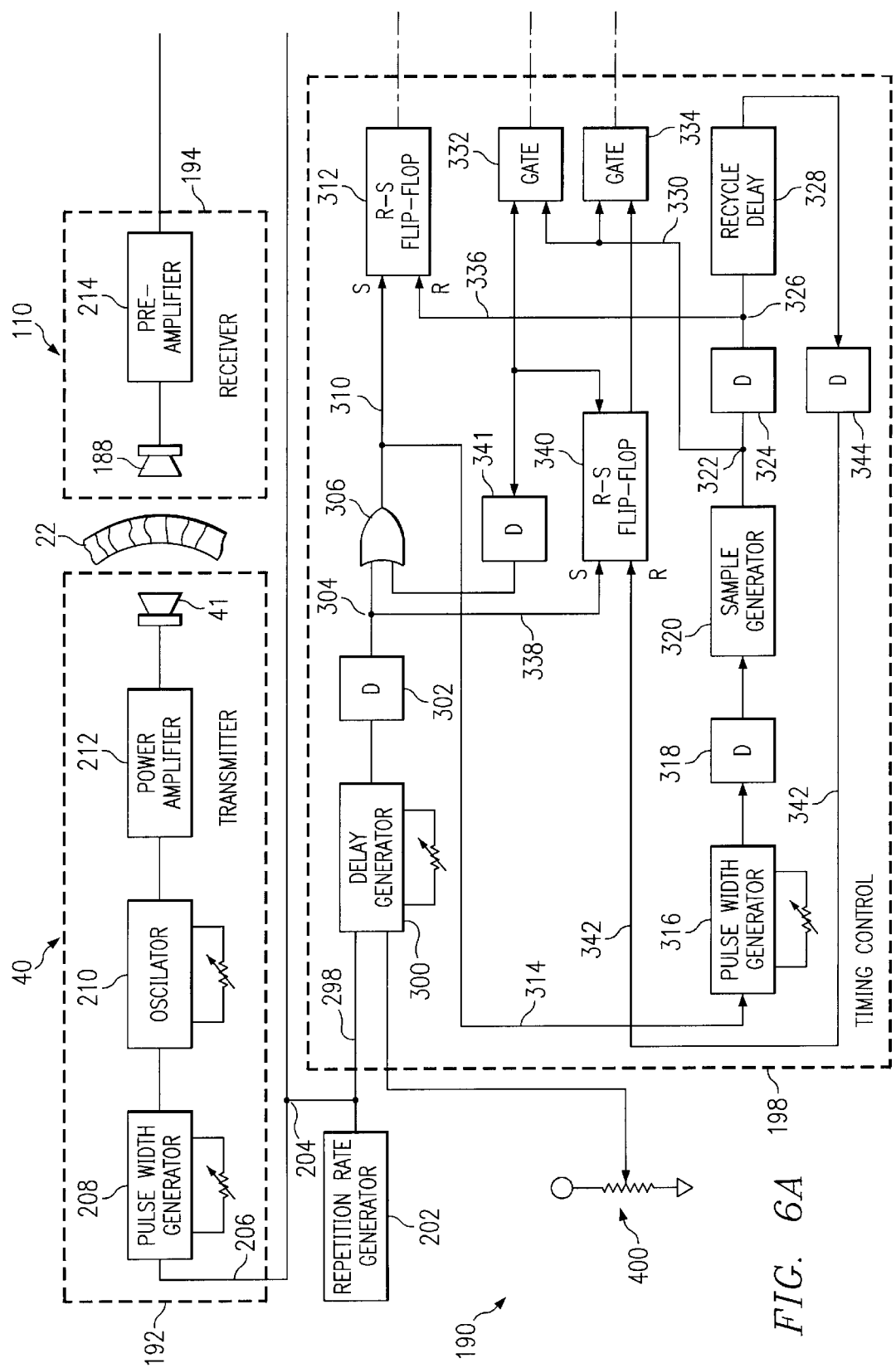
FIG. 6A is a schematic drawing showing portions of a block diagram of various electronic components and electrical circuits associated with the tire inspection equipment of FIG. 1.
Figure 6B:
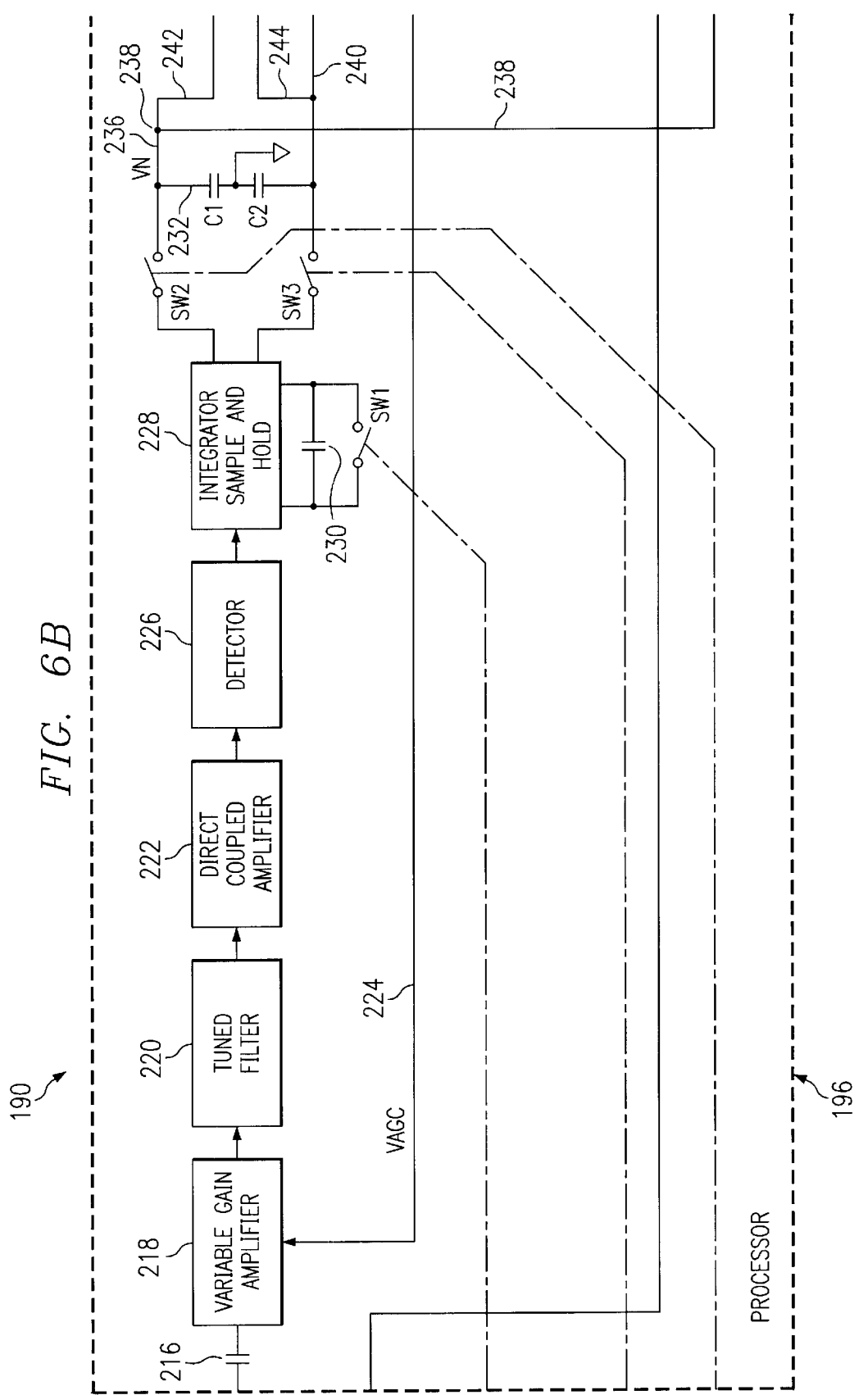
FIG. 6B is a schematic drawing showing portions of a block diagram of various electronic components and electrical circuits associated with the tire inspection equipment of FIG. 1.
Figure 6C:
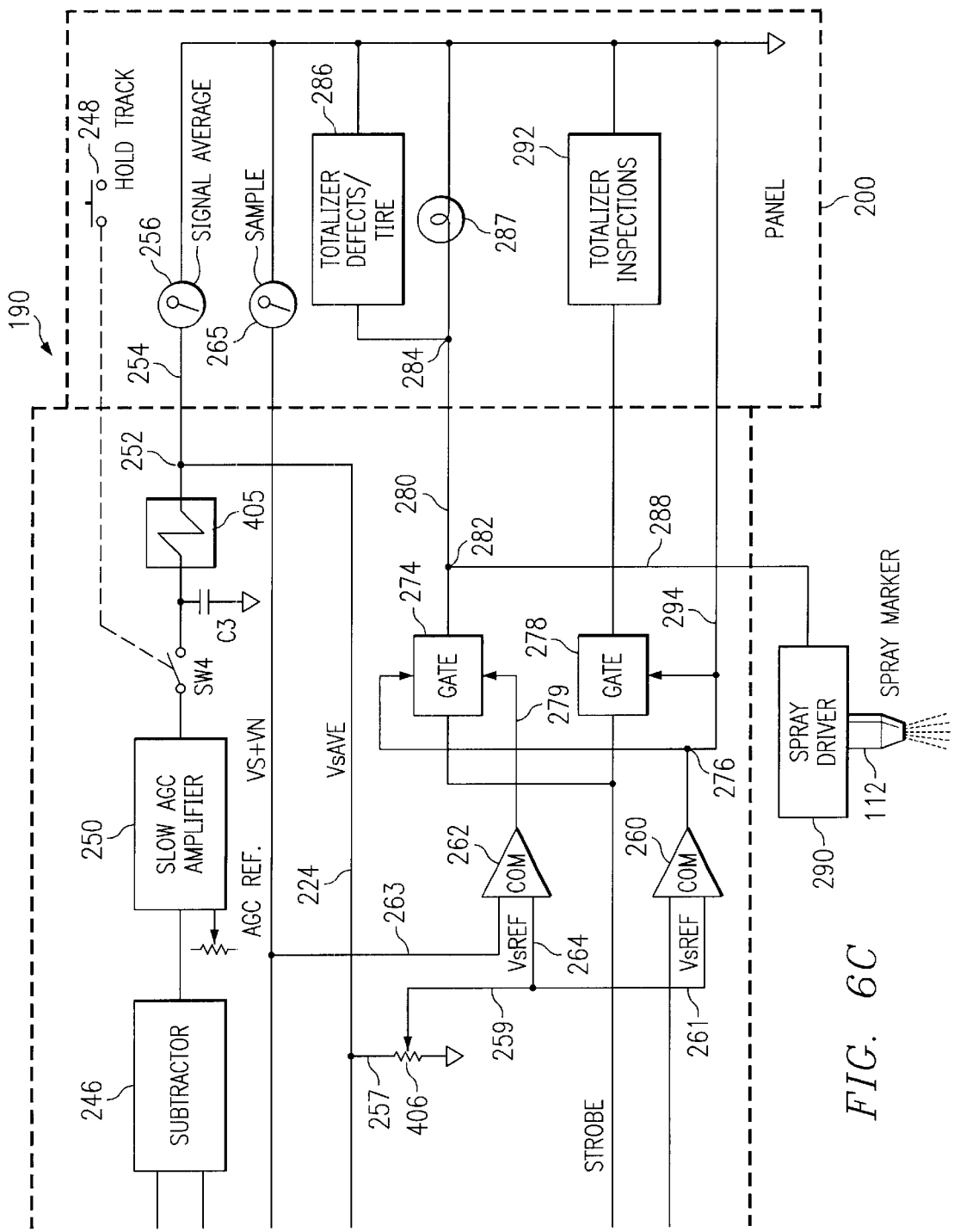
FIG. 6C is a schematic drawing showing portions of a block diagram of various electronic components and electrical circuits associated with the tire inspection equipment of FIG. 1.
Figure 7:
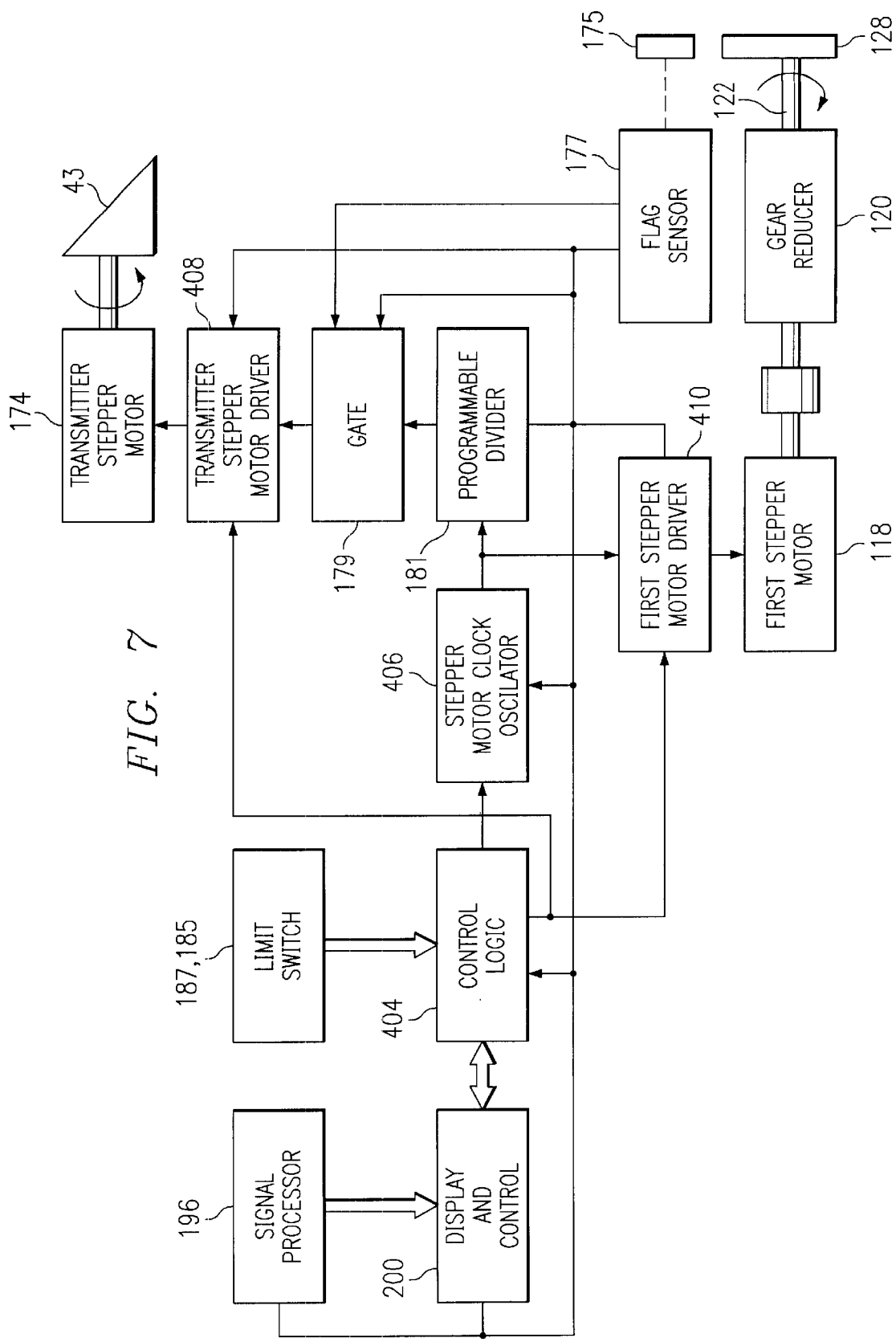
FIG. 7 is a schematic drawing showing a block diagram of a control circuit for a stepper motor used with the tire inspection equipment of FIG. 1.

Electrical circuit 190 as shown in FIGS. 6A, 6B and 6C will generate and process electrical data in response to a portion of each burst of collimated acoustic energy passing through tire 22. Most of the electrical components associated with electrical circuit 190 are preferably contained within second housing 160. Second housing 160 may also be referred to as an "electronic console" or a "control console." Electrical components shown in FIGS. 6A, 6B, and 6C may be obtained from various sources including Trienco, Inc. located in Montrose, Colo.

Second housing 160, as shown in FIG. 1, includes a generally hollow, enclosed structure mounted on rollers 162. Second housing 160 may be described as an enclosed, sealed cabinet which protects various components associated with electrical circuit 190 from contamination and vibration associated with rotating and inspecting tire 22. Second housing 160 is preferably connected with first housing 124 by flexible electrical cable 164. Second housing 160 is substantially smaller than first housing 124. Rollers 162 and electrical cable 164 cooperate with each other to allow positioning second housing 160 as desired for operation of tire inspection equipment 20.

Figure 8:
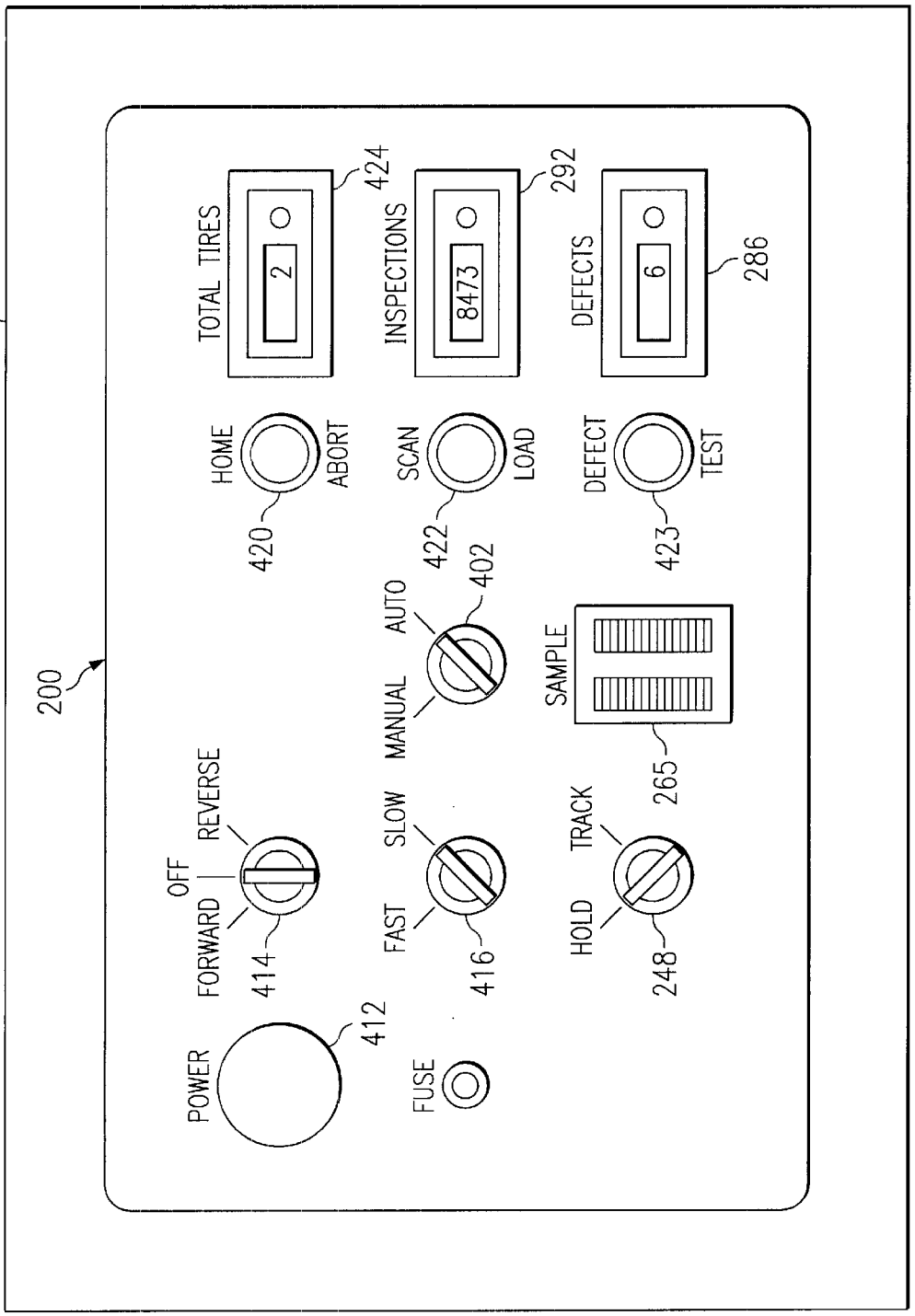
FIG. 8 is a schematic drawing showing a control panel for a remotely located electronic control console incorporating teachings of the present invention.

Second housing 160 preferably includes lid or cover 166 which may be opened to allow access to the various electrical components disposed therein. Display and control panel 200 as shown in FIG. 8 is preferably disposed on the top of lid 166. Additional cover plates and/or drawers (not expressly shown) may be provided in second housing 160 to provide access to various electronic components associated with electrical circuit 190. When lid 166 is closed as shown in FIG. 1 and any other drawers or covers are closed, second housing 160 will preferably provide a sealed environment to protect the electronic components from the environment associated with a tire retreading facility.

Electrical circuit 190, transmitter transducer section 192, receiver transducer section 194, processor 196, inspection timing control section 198 and display and control panel 200 are electrically connected with each other as shown in FIGS. 6A, 6B and 6C. Details concerning the design and operation of these electrical circuits may be found in U.S. Pat. No. 4,936,138. Tire inspection equipment incorporating teachings of the present invention may be used with a wide variety of other electrical control systems and is not limited to use with electrical circuit 190 or any of the other electrical components shown in FIGS. 6A, 6B and 6C.

Repetition rate generator 202 is preset to produce a pulse output rate sufficiently high to assure adequate density of inspection areas 46. This pulse is furnished to junction 204 from which it is supplied via lead 206 to pulse width generator 208 in transmitter section 192 whose output enables oscillator 210. Oscillator 210 drives power amplifier 212 with a sufficient number of cycles to allow transmitter transducer 41 to build up to maximum output and produce a burst of energy directed by mirror 43 to illuminate a selected area of the inner surface of tire 22.

In receiver section 194, receiver transducer 188 receives a small amount of the transmitted energy passing through tire 22 along with ambient noise. The resulting noise only or signal plus noise voltage from receiver transducer 188 is amplified by a preamplifier 214. In processor section 196 the output from preamplifier 214 is furnished through capacitor 216 to variable gain amplifier 218 and then through tuned filter 220 to a fixed gain direct coupled amplifier 222 to further amplify the signal plus noise in accordance with an automatic gain control AGC voltage applied via feedback lead 224 to variable gain amplifier 218. Detector 226 receives the amplified noise only (VN) or signal plus noise (VS+VN) voltage and applies a rectified voltage to integrator 228. Integrator 228 has an enable FET switch SW1 in parallel with capacitor 230 whose closing member is connected through timing control circuit 198 to repetition rate generator 202. After an appropriate delay from the repetition rate generator caused by the delay generator 300, the enable SW1 is caused to open twice, permitting integration of (1) the ambient amplified noise voltage just prior to the signal arrival time; and (2) the amplified signal plus ambient noise voltage during the signal arrival time.

Integrator 228 has two output leads-connected to one terminal of an FET switch SW2 and an FET switch SW3 respectively. The output terminals of these switches are interconnected by lead 232 having a pair of capacitors C1 and C2 connected to ground. Field effect switches SW2 and SW3 along with capacitors C1 and C2 and appropriate high input impedance buffer amplifiers (not shown) comprise a dual channel hold circuit holding both the integrated VN voltage and the integrated VS+VN voltage. The output terminal for the switch SW2 is connected via lead 236 to another terminal 238. The voltage (VN) at this terminal from SW2 represents the noise factor while the voltage (VS+VN) at terminal 240 from SW3 is equivalent to signal plus noise. One pair of leads 242 and 244 are connected from terminals 238 and 240 to a subtractor circuit 246 whose output produces a voltage (VS) equivalent to signal only and is connected to slow AGC amplifier 250 which provides the feedback AGC control signal. The resulting long time averaged voltage from amplifier 250 is almost solely due to the received and integrated VS only. The feedback AGC signal is connected to the normally closed Hold/Track AGC switch SW4 and in normal operation to voltage follower 405. The feedback AGC voltage from voltage follower 405 is furnished to variable gain amp 218 via lead 224, and it also provides an output connected through a terminal 252 via a lead 254 to a "signal average" indicator 256 on display panel 200.

Branching from AGC output lead 224 to variable gain amplifier 218 is lead 257 connected to threshold potentiometer 406. The wiper of potentiometer 406 is connected via lead 259 to the inputs of comparators 262 and 260 and thus establishes a reference input voltage (VS Ref.) to comparators 262 and 260 which may be adjusted, via threshold potentiometer 406, to be any fraction of the average VS voltage.

With the VS Ref. voltage established at one input of comparator 260, and the integrated, sampled, and held VN voltage at the other input, comparator 260 will produce an output when VN exceeds VS Ref. whenever there is a long term of signal loss or excessive ambient noise. This output in turn opens gates 274 and 278 disallowing any output from gate 274 to a defect totalizer and from gate 278 to an inspection totalizer upon the arrival of the strobe pulse.

With VS Ref. established at one input of comparator 262 and integrated, sampled, and held VS+VN voltage at the other input, comparator 262 will produce an output when VS and VN does not exceed VS ref (when a defect is sensed), which is a fraction of the long term derived VS average.

The output of comparator 262, in turn, will close gate 274 (if no output was provided by comparator 260) and upon arrival of the strobe pulse gate 274 will output a pulse to increment the defect totalizer 286.

Lead 258 from the VN terminal 238 is furnished as one input to a first comparator 260 whose other input 261 is connected to a VS Ref. Similarly, lead 263 from the (VS+

VN) terminal 240 is furnished to a second comparator 262 which has another input 264 connected to a VS Ref. A second lead from (VS+VN) is furnished to real time sample indicator 265. The output from comparator 262 is supplied to a gate 274. The output from comparator 260 is supplied through a terminal 276 to gate 274 and to a gate 278.

In the timing control circuit 198 the output from the repetition rate generator 202 is furnished via lead 298 to an adjustable delay generator 300 which is controlled by a potentiometer 400 to provide a time delay corresponding to the varying time of travel for an ultrasonic signal from the transmitter assembly 40 to the receiver assembly 110. As previously noted, linear potentiometer 400 is mechanically connected with control arm 142 to produce a voltage change proportional to any change in the distance between transmitter assembly 40 and receiver assembly 110 as follower 138 moves through groove 151 or 152. The output from delay generator 300 is supplied to a differentiator 302 whose output is connected through a terminal 304 to an "OR" gate 306.

The output of "OR" gate 306 is connected to a terminal 308 from which extends a lead 310 connected to "S" input of an R-S flip-flop 312 whose output is connected to operate SW1 of the integrator 228. Another lead 314 from the output terminal of "OR" gate 306 is connected to a pulse width generator 316. The output of the pulse width generator is furnished to a differentiator 318 whose output is supplied to a sample generator 320. The output from the sample generator is supplied through a terminal 322 to a differentiator 324 and through another terminal 326 to a recycle delay 328. A lead 330 from the terminal 322 is connected to a pair of gates 332 and 334. A lead 336 from the output terminal 326 of the differentiator 324 is connected to the "R" input for the flip-flop 312.

A lead 338 from the output terminal 304 for the differentiator 302 is supplied to the "S" input of an RS flip-flop 340 to put it in its set state. The "R" input to this flip-flop is provided via a lead 342 through a differentiator 344 whose input is provided from the recycle delay 328. One output from the flip-flop 340 is furnished to the gate 334 and another output is furnished to the gate 332 as well as through a differentiator 341 to the "OR" gate 306.

The operation of the electrical circuit 190 may be summarized as follows with reference to FIGS. 6A, 6B and 6C and FIG. 7. When a single pulse is provided by the repetition rate generator 202 to the terminal 204 it travels to the transmitter circuit so that the transmitter assembly 40 is activated as previously described to produce a burst of acoustic energy directed normally to the inside surface of tire 22. The repetition rate generator pulse is also provided to the timing control section 198 to trigger the delay generator 300. This produces a pulse of a predetermined length (which is proportional to the distance between transmitter assembly 40 and receiver assembly 110 and thus the time of travel of the ultrasonic pulse between them). The trailing edge of the pulse from the delay generator is differentiated by element 302 to produce a pulse which: (1) sets the R.S. flip-flop 340 and (2) passes through the "OR" gate 306 to set the R.S. flip-flop 312. When R.S. flip-flop 312 is set, it opens SW1 and enables the integrator 228 so that it will commence integrating.

The output from "OR" gate 306 supplied to R.S. flip-flop 312 is simultaneously supplied to pulse width generator 316 which produces a timing pulse of a predetermined length whose trailing edge is differentiated by element 318 and supplied to the sample generator 320. The output from this sample generator is furnished to gate 334 which provides a signal that closes SW2 and causes the integrator 228 to supply the integrated voltage (VN) equivalent to noise only to capacitor C1. The output from the sample generator is also differentiated by element 324 is also furnished to the recycle delay element 328 which provides a predetermined time space between first and second integrations during a single cycle. The output from the recycle delay 328 is differentiated by element 344 and is supplied to the R.S. flip-flop 340 causing it to reset and provide an output that (1) activates gate 332 which in turn closes SW3 on the integrator 228 causing a second integration for signal plus noise (VS+VN) to commence; and (2) simultaneously provides a differentiated signal through "OR" gate 306 to the R.S. flip-flop 312 to again open SW1 and enable the integration. Thus, in this second integration a voltage value for signal plus noise is stored and held in capacitor C2. At the trailing end of the second sample generator pulse, the differentiator 324 again produces a signal which terminates the second integration.

During each inspection cycle the noise only integration voltage at terminal 238 and the signal plus noise integration voltage at terminal 240 are supplied to the subtractor circuit 246 which may be a conventional operational amplifier. The output of the subtractor is supplied as one input to the slow AGC amplifier 250 which functions to filter out any rapid cycle changes and provides an output signal that is substantially amplitude constant but which changes slowly in response to signal variations. The output from this AGC amplifier is furnished via the hold/track circuit: (1) to the indicator 256 on the display panel which provides a visual means for observing signal variations during an inspection cycle; as a feedback signal to the variable gain amplifier 218 via lead 224 to maintain stability with the received test signal; and (2) as an input to the threshold potentiometer 406.

If there is excessive ambient noise around the apparatus during a test cycle, a voltage from the noise only integration terminal will be supplied via lead 258 to comparator 260. This comparator has a signal level reference voltage which is a fraction, e.g., 80% of the VS average voltage and will produce an output if the integrated noise voltage exceeds the reference voltage. The output of comparator 260 disables gates 274 and 278 to turn off the apparatus if excess noise is present which would negate the effectiveness of an inspection cycle.

Now, assuming that excess ambient noise is not present and integrated signal only voltage (VS) is producing a stable AGC amplifier, the signal plus noise (VS+VN) is supplied to comparator 262. Here, the ref. voltage is maintained at a value which is preset to a level which is a fraction, e.g., 80% of the average signal. If, during one of the ultrasonic pulses in an inspection cycle, a possible defect such as delamination in tire 22 is encountered, the integrated VS+VN signal will fall producing an output from the comparator 262 and thereby indicating a possible defect in tire 22. This comparator output is supplied to gate 275 which (1) furnishes a signal to the display panel 200 that activates the defects counter 286 and the indicator lamp 287; and (2) furnishes a signal via lead 288 to the spray delay 290. This calibrated delay allows the rotation of tire 22 to carry the detected defect from the proximity of the receiver 16 to the proximity of the spray marker 20. The delayed signal then activates spray marker 112, causing a marking substance to be sprayed onto tire 22 in the near vicinity of the possible defect.

Display and control panel 200 is provided on electronic console 160 to allow control of tire inspection equipment 20 and recording the results of each inspection cycle. As shown in FIG. 8, display and control panel 200 includes power ON switch 412, a forward-reverse selector 414, a fast-slow selector 416 and the hold-track control 248 in addition to the manual-auto switch button 402, and switch buttons for home-abort 420, scan-load 422 and defect-text 423. Indicators are also provided for showing the number of tires inspected 424, the number of pulsed inspections for one inspection cycle 292 and the number of defects detected during the cycle 286. Other recorded instruments well known in the art could be connected to the display unit to provide readable printouts of test results where desired.

For some applications, power ON switch 412 and/or scan switch 422 may be placed on the extreme end of supporting beam 144 extending from second bulkhead 148. Also, one or more of the switches on control panel 200 may be placed within housing 160. For example, the hold track button or other buttons which are normally only used by service personnel may preferably be placed within housing 160.

Display and control panel 200 along with electrical circuit 190 allows tire inspection equipment 20 to either automatically or manually scan tire 22. After tire 22 has been loaded onto roller shafts 52, scan switch 422, as shown on control panel 200, may be actuated. This causes control logic 404 to:
actuate bead spreader mechanism 68 and 70;
start tire rotation motor 64;
start stepper motor clock oscillator 406;
start first stepper motor driver 410 and second stepper motor driver 408 to drive them in a forward or clockwise motion; and
enable signal processor 196.

Pressing scan switch 422 will also deactivate lift assembly 38.

At each clock pulse from the clock oscillator, first stepper motor drive 410 causes first stepper motor 118 to advance 1.8°. In the embodiment shown and described, the 30:1 gear reducer 120 in turn reduce the actual angular change to 0.060° per clock oscillator pulse. Since the clock oscillator is operating about eighteen (18) pulses per second, control arm 142 will traverse its one hundred and eighty degree arc in about 2.8 minutes. In actual operation, control arm 142 may be allowed to travel somewhat beyond the horizontal centerline of tire 22 for a total travel of 200°, yielding a total inspection time of three minutes.

As shown in FIG. 5, the required angular relationship between the mirror 43 and control arm 142 as tire 22 is transversed, must take into account that: (1) control arm 142 and mirror 43 must be angularly aligned when intercepting-the horizontal cross section of tire 22; (2) transmitter mirror angle (B) must progressively increase faster than control arm angle (A) as the sidewall is scanned; (3) the transmitter mirror angle (B) must suddenly be caused to be less than control arm angle (A) after the corner on track 150 is turned; (4) the transmitter mirror angle (B) must equal control arm angle (A) at the tread center line and increase faster than control arm angle (A) from the tread centerline to a corner; and (5) after each corner turn, transmitter mirror angle (B) must suddenly be caused to be less than control arm angle (A) and then must progressively increase faster than control arm angle (A) until the horizontal cross section axis of tire 22 is reached. The required angular relationship between transmitter mirror 43 and control arm 142 is accomplished with the use of a programmable divider 173, a system of flags 175, flag sensor 177, gate 179, transmitter stepper motor driver 408 and transmitter or second stepper motor 174.

The field programmable divider 173, typically set to divide the stepper motor clock oscillator output by 28:1, produces an effective rotation of the 1.8° per step transmitter stepper motor 174 of 1.8 divided by 28 which equals 0.064 degrees per clock oscillator 406 output pulse. Therefore, the transmitter mirror angle (B) gains approximately 0.064 minus 0.060 or 0.004 degrees over control arm 142 assembly angle and upon each clock oscillator output pulse and produces the required leading transmitter mirror angle (B) shown in FIG. 5. Near each corner of tire 22, where receiver assembly 110 is rapidly rotated by its complete track 151 or 152, flag 175, mounted on track 150, is sensed by flag sensor 177. Flag sensor 177 may be of the retro-reflective type which produces a light beam directed at track 150. When the beam strikes a flag 175, flag sensor 177 produces an output signal. The flag sensor output is furnished to a gate 179 which controls transmitter stepper motor 174. Thus, flags 175 function to temporarily inhibit transmitter stepper motor 174 while control arm 142 continues to rotate during each inspection cycle, until control arm 142 angle (A) exceeds angle (B) of mirror 43 and the transmitter stepper motor 174 is again enabled so that movement of mirror 43 is properly coordinated with receiver assembly 110.

When the scan (visualized left to right in FIG. 5) has been completed after the clockwise traverse, a clockwise limit switch 187 is encountered by a photocell or opto switch mounted on plate 154. Control logic 404, in turn, reverses the direction of stepper motors 118 and 174 and accelerates stepper motor clock oscillator 406 to produce a rapid return of control arm 142 and transmitter assembly 40 until a counterclockwise limit switch 185 is encountered by another photocell or opto switch mounted on plate 154. Control logic 404 will then stop rotation of tire 22 to permit unloading tire 22.

Although the present invention and its advantages have been described in detail it should be understood that various changes, substitutions, and alterations can be made hereto without departing from the spirit and scope of the invention as defined by the following claims.

What is claimed is:
1. Apparatus for inspecting a tire having an interior surface and an exterior surface comprising:
a transmitter assembly for directing energy against the interior surface and through the tire while the tire rotates during an inspection cycle;
a receiver assembly operable to detect energy which passes through the tire from the transmitter assembly;
mechanical and electrical systems for supporting and rotating the tire during an inspection cycle and for controlling movement of the transmitter assembly and the receiver assembly while maintaining a desired distance between the transmitter assembly, the receiver assembly and the tire as the tire rotates;
the mechanical system including both a tire supporting and rotating assembly attached to and extending from a housing and a receiver control assembly attached to and extending from the housing;
the tire supporting and rotating assembly spaced from the receiver control assembly;
a bulkhead releasably secured to the housing;
a first supporting beam, a second supporting beam, and a third supporting beam with one end of each supporting beam secured to the bulkhead; and
mechanical components of the single receiver control assembly slidably disposed on the first, second and third supporting beams.

2. The apparatus of claim 1 further comprising a single stroke lever to adjust linear movement of the transmitter assembly and the receiver assembly relative to each other during an inspection cycle.

3. The apparatus of claim 1 wherein the receiver control system further comprises:
a first plate slidably mounted on the first supporting beam;
a first stepper motor mounted on the first plate;
a U-shaped track slidably mounted on the second supporting beam;
a bearing slidably mounted on the third supporting beam;
an output shaft extending from the first stepper motor to the bearing assembly slidably mounted on the third supporting beam;
a linear bearing assembly attached to the output shaft; and
a control arm attached to and extending from the linear bearing assembly towards the tire supporting and rotating assembly.

4. The apparatus of claim 1 further comprising the receiver control assembly having a single control arm extending from the receiver control assembly toward the tire supporting and rotating assembly.

5. The apparatus of claim 1 further comprising:
a linear bearing assembly slidably disposed within the tire supporting and rotating assembly; and
a carriage assembly attached to the linear bearing assembly with the transmitter assembly mounted on the carriage assembly.

6. The apparatus of claim 5 further comprising a rack and pinion assembly for moving the carriage assembly and the transmitter assembly linearly within the tire supporting and rotating assembly.

7. Apparatus for inspecting a tire comprising:
a first housing and a second housing;
a transmitter assembly for directing energy against an interior surface and through the tire as the tire rotates during an inspection cycle;
a receiver assembly to detect energy from the transmitter assembly which passes through the tire;
mechanical and electrical systems for supporting and rotating the tire during an inspection cycle and for controlling movement of the transmitter assembly and the receiver assembly relative to each other and the tire so that energy will be directed through the tire as it rotates while maintaining a desired distance between the transmitter assembly and the receiver assembly;
the mechanical system including both a tire supporting and rotating assembly attached to and extending from the first housing and a receiver control assembly attached to and extending from the first housing;
portions of the electrical system disposed in the second housing remotely located from the first housing; and
only a flexible electric cable connecting the second housing with the first housing.

8. Apparatus for inspecting a tire comprising:
a transmitter assembly for directing energy against a tire surface and through the tire;
a receiver assembly operable to detect energy which passes through the tire from the transmitter assembly;
mechanical and electrical systems for supporting and rotating the tire during an inspection cycle and for controlling movement of the transmitter assembly and the receiver assembly relative to each other while maintaining a desired distance between the transmitter assembly, the receiver assembly, and the tire;
mechanical components of the receiver control assembly slidably disposed on supporting beams extending from a housing; and
a single stroke lever to adjust movement of the transmitter assembly and the receiver assembly relative to each other during an inspection cycle of the tire.

9. An apparatus for inspecting a tire comprising:
a housing;
a transmitter assembly for directing energy against an interior surface of the tire and through the tire as the tire rotates during an inspection cycle;
a receiver assembly to detect energy which passes through the tire from the transmitter assembly;
a tire supporting and rotating assembly attached to and extending from the housing;
a receiver control assembly attached to and extending from the housing;
the receiver control assembly having a single control arm extending therefrom for supporting the receiver assembly and coordinating movement of the receiver assembly relative to the transmitter assembly during an inspection cycle; and
a first stepper motor for rotating the single control arm and a second stepper motor for rotating a mirror within the transmitter assembly.

10. The apparatus of claim 9 further comprising:
a generally inverted U-shaped track with at least one groove formed therein;
the U-shaped track secured to and forming a part of the receiver control assembly; and
a follower extending from one end of the control arm for engagement with the groove during movement of the control arm.

11. The apparatus of claim 9 further comprising limit switches for controlling movement of the single control arm through an arc of at least one hundred eighty degrees during each inspection cycle.

12. The apparatus of claim 9 further comprising a rack and pinion assembly for controlling movement of the receiver assembly in cooperation with movement of the single control arm.

13. An apparatus for inspecting a tire comprising:
mechanical and electrical systems for supporting and rotating the tire during an inspection cycle;
a transmitter assembly for directing energy through the tire as the tire rotates during an inspection cycle;
a receiver assembly to detect energy which passes through the tire from the transmitter assembly;
the mechanical and electrical systems controlling movement of the transmitter assembly and the receiver assembly to substantially maintain a desired distance between the transmitter assembly, the receiver assembly and the tire during an inspection cycle;
the mechanical system including both a tire supporting and rotating assembly and a receiver control assembly;
the receiver control assembly having a generally U-shaped track remotely located from the tire supporting and rotating assembly;
a control arm having a first end with the receiver assembly attached thereto; and the control arm having a second end with a follower extending therefrom and engaged with a groove in the generally U-shaped track.

14. Apparatus for inspecting a tire comprising:

a housing;

a transmitter assembly for directing energy through the tire during an inspection cycle;

a receiver assembly to detect energy from the transmitter assembly which passes through the tire;

mechanical and electrical systems for supporting and rotating the tire during an inspection cycle and for controlling movement for the transmitter assembly and the receiver assembly while maintaining a desired distance between the transmitter assembly and the receiver assembly and the tire;

the mechanical system including both a tire supporting and rotating assembly and a receiver control assembly;

the tire supporting and rotating assembly including a first bulkhead releasably secured to the housing;

a pair of roller shafts extending from the first bulkhead with the transmitter assembly disposed between the roller shafts;

the receiver control assembly including a second bulkhead releasably secured to the housing and spaced from the first bulkhead;

a first supporting beam, a second supporting beam and a third supporting beam with one end of each supporting beam secured to the second bulkhead; and mechanical components of the receiver control assembly slidably disposed on the first, second and third supporting beams.

* * * * *